US011717484B2

(12) United States Patent
Yadav et al.

(10) Patent No.: US 11,717,484 B2
(45) Date of Patent: Aug. 8, 2023

(54) TOPICAL TREATMENT OF INFLAMMATORY BOWEL DISEASE USING ANTIBODIES AND FRAGMENTS THEREOF

(71) Applicants: Tillotts Pharma AG, Rheinfelden (CH); University College London, London (GB)

(72) Inventors: Vipul Yadav, London (GB); Abdul Waseh Basit, Middlesex (GB); Felipe José Oliveira Varum, Rheinfelden (CH); Roberto Carlos Bravo Gonzaléz, Rheinfelden (CH); Esther Maria Furrer, Rheinfelden (CH)

(73) Assignees: Tillotts Pharma AG, Rheinfelden (CH); University College London, England (GB)

( * ) Notice: Subject to any disclaimer, the term of this patent is extended or adjusted under 35 U.S.C. 154(b) by 485 days.

(21) Appl. No.: 16/616,460

(22) PCT Filed: Apr. 26, 2018

(86) PCT No.: PCT/EP2018/060690
§ 371 (c)(1),
(2) Date: Nov. 23, 2019

(87) PCT Pub. No.: WO2018/219559
PCT Pub. Date: Dec. 6, 2018

(65) Prior Publication Data
US 2020/0170956 A1    Jun. 4, 2020

(30) Foreign Application Priority Data
May 31, 2017   (EP) .................... 17173847

(51) Int. Cl.
*A61K 9/28*    (2006.01)
*A61K 9/00*    (2006.01)
*C07K 16/24*   (2006.01)

(52) U.S. Cl.
CPC ............ *A61K 9/288* (2013.01); *A61K 9/0031* (2013.01); *A61K 9/0053* (2013.01); *C07K 16/241* (2013.01); *C07K 2317/21* (2013.01); *C07K 2317/24* (2013.01); *C07K 2317/55* (2013.01)

(58) Field of Classification Search
None
See application file for complete search history.

(56) References Cited

U.S. PATENT DOCUMENTS 8,647,626 B2    2/2014   Fox
2010/0129377 A1  5/2010  Van Neerven

OTHER PUBLICATIONS

Tashima et al. 'Delivery of Orally Administered Digestible Antibodies Using Nanoparticles.' Int. J. Mol. Sci. 2021, 22(7), 3349; https://doi.org/10.3390/ijms22073349.*
https://www.accessdata.fda.gov/drugsatfda_docs/label/2002/adalabb123102lb.htm 2002.*
Nugent et al. 'Intestinal luminal pH in inflammatory bowel disease: possible determinants and implications for therapy with aminosalicylates and other drugs.' Gut 48:571-577, 2001.*
Bhol, K. et al., "AVX-470: A Novel Oral Anti-TNF Antibody with Therapeutic Potential in Inflammatory Bowel Disease", *Inflammatory Bowel Disease*, vol. 19, No. 11, pp. 2273-2281 (Oct. 1, 2013).
Carter, P.J., "Potent Antibody Therapeutics By Design", J. Immuno., vol. 6, pp. 343-357 (Apr. 7, 2006).
Hartman, D. et al., "Effects of AVX-470, an Oral, Locally Acting Anti-Tumour Necrosis Factor Antibody, on Tissue Biomarkers in Patients with Active Ulcerative Colitis", *J. Crohn's Colitis*, vol. 10, No. 6, pp. 641-649 (Jan. 22, 2016).
Kuo, Timothy et al., "Neonatal Fc Receptor: From Immunity to Therapeutics", J. Clin. Immunol., vol. 30, No. 6, pp. 777-789 (Oct. 1, 2010).
Nugent, S.G. et al., "Intestinal Luminal pH in Inflammatory Bowel Disease: Possible Determinants and Implications for Therapy with Aminosalicylates and Other Drugs", Gut, vol. 48, pp. 571-577 (Apr. 1, 2001).
Rodewald, R., "pH-Dependent Binding of Immunoglobulins to the Intestinal Cells of the Neonatal Rat", *J. Cell Bio.*, vol. 71, No. 2, pp. 666-669 (Nov. 1, 1976).
Yadav, Vipul et al., "Gastrointestinal Stability of Therapeutic Anti-TNF [alpha] IgG1 Monoclonal Antibodies", *Int. J. of Pharmaceutics*, vol. 502, No. 1, pp. 181-187 (Feb. 15, 2016).

* cited by examiner

*Primary Examiner* — Nora M Rooney
(74) *Attorney, Agent, or Firm* — Smith Patent, LLC; Chalin A. Smith

(57) ABSTRACT

The present invention relates to the therapeutic uses of compositions containing antibody molecules and functional fragments thereof, e.g antibody molecules and functional fragments capable of binding to tumor necrosis factor alpha (TNFα), in the topical treatment of inflammatory bowel diseases, including Crohn's disease and ulcerative colitis.

13 Claims, 17 Drawing Sheets

A.

B.

C.

D.

A.

B.

A.

B.

C.

D.

A.

B.

C.

D.

A.

B.

C.

D.

TOPICAL TREATMENT OF INFLAMMATORY BOWEL DISEASE USING ANTIBODIES AND FRAGMENTS THEREOF

PRIORITY

This application corresponds to the U.S. National Phase of International Application No. PCT/EP2018/060690, filed Apr. 26, 2018, which, in turn, claims priority to European Patent Application No. 17.173847.9 filed May 31, 2017, the contents of which are incorporated by reference herein in their entirety.

FIELD OF THE INVENTION

The present invention relates to the therapeutic use of compositions containing antibody molecules and functional fragments thereof, e.g antibody molecules and functional fragments capable of binding to tumor necrosis factor alpha (TNFα), in the topical treatment of inflammatory bowel diseases, including Crohn's disease and ulcerative colitis.

BACKGROUND

Inflammatory bowel disease (IBD) is the collective term for a number of chronic disorders of the gastrointestinal tract, including Crohn's disease (CD) and ulcerative colitis (UC). CD and UC, while constituting distinct conditions share several symptoms, including recurrent episodes of inflammation of the gastrointestinal wall. These cycles of inflammation are characterized by elevated levels of soluble and membrane-bound forms of the pro-inflammatory cytokine tumor necrosis factor alpha (TNFα) in the affected tissue. TNFα is released by and interacts with cells of the immune system and is thought of as a key factor in the signaling cascade that results in inflammation. The use of TNFα-specific antibodies for the neutralization of TNFα molecules is an established treatment for Crohn's disease and ulcerative colitis as discussed e.g. in Talley et al. (The American Journal of GASTROENTEROLOGY, 106, Supplement 1,2011), Feldman et al. (Transplantation Proceedings, 30, 4126-4127, 1998) and Adorini et al. (Trends in Immunology Today, 18, 209-211, 1997).

Several monoclonal antibodies against TNFα have been described in the prior art. Meager et al. (Hybridoma, 6, 305-311, 1987) describe murine monoclonal antibodies against recombinant TNFα. Fendly et al. (Hybridoma, 6, 359-370, 1987) describe the use of murine monoclonal antibodies against recombinant TNFα in defining neutralising epitopes on TNF. Furthermore, in international patent application WO 92/11383, recombinant antibodies, including CDR-grafted antibodies, specific for TNFα are disclosed. U.S. Pat. No. 5,919,452 discloses anti-TNFα chimeric antibodies and their use in treating pathologies associated with the presence of TNFα. Further anti-TNFα antibodies are disclosed in Stephens et al. (Immunology, 85, 668-674, 1995), GB-A-2 246 570, GB-A-2 297 145, U.S. Pat. No. 8,673,310, US 2014/0193400, EP 2 390 267 B1, U.S. Pat. Nos. 8,293,235, 8,697,074, WO 2009/155723 A2 and WO 2006/131013 A2.

Currently approved anti-TNFα biotherapeutics include (i) infliximab, a chimeric IgG anti-human monoclonal antibody (Remicade®); (ii) etanercept, a TNFR2 dimeric fusion protein, with an IgG1 Fc (Enbrel®); (iii) adalimumab, a fully human monoclonal antibody (mAb) (Humira®), (iv) certolizumab, a PEGylated Fab fragment (Cimzia®) and (v) Golimumab, a human IgGIK monoclonal antibody (Simponi®). Moreover, various biosimilars are in development, and a mimic of infliximab known as Remsima has already been approved in Europe.

At present, the standard therapy for the treatment of inflammatory bowel diseases like CD or UC using TNFα-specific antibodies involves the regular systemic administration of a TNFα antibody by intravenous infusion or subcutaneous injection. The intravenous administration can give rise to complications including acute infusion reaction, hypersensitivity and anaphylactic shock. Moreover, this systemic application of an immunosuppressant bears a multitude of risks associated with the systemic inhibition of the immune defense function of TNFα in the patient, including for example infectious complications. Finally, the systemic application is known to lead to the build-up of antibodies specific to anti-TNFα antibody in the body of the patient, resulting in a loss of response to the treatment. Currently, there are no commercial therapies available involving the oral or rectal administration of a composition containing a TNFα-specific antibody for the topical application.

Bhol et al. (2013) Inflamm Bowel Dis. 19(11): 2273-2281 describe the oral administration of anti-TNF antibodies to mice either before or after induction of colitis. U.S. Pat. No. 8,647,626 B2 discloses compositions comprising TNF-specific antibodies for oral delivery. WO 2011/047328 describes antibody therapeutics with local activity in the digestive tract.

There exists a need for an alternative treatment of inflammatory bowel diseases such as CD or UC with anti-TNFα antibodies or functional fragments thereof, allowing a better targeting of inflamed tissues in the gastrointestinal tract. The treatment should particularly enable the effective penetration of the antibody or fragment thereof into the inflamed gastrointestinal wall.

SUMMARY OF THE INVENTION

Surprisingly it has been found by the present inventors that the provision of a TNFα antibody or a functional fragment thereof to the luminal side of the large intestinal wall at a lower than normal pH results in its effective permeation across the large intestinal wall. It has been found that a lower pH of about 6 results in an increased uptake of TNFα antibodies or functional fragments thereof across the epithelial and into the mucosal layer of the large intestinal wall, as well a deeper penetration into submucosal layer of the large intestinal wall, than a higher pH of about 7.4. It has also been found by the present inventors that the local concentration of the TNFα antibody or functional fragment thereof directly correlates with the amount of the TNFα antibody or functional fragment thereof taken up by the large intestinal wall. Where the protective mucus layer of the gastrointestinal wall is impaired, the TNFα antibody or functional fragment thereof is taken up faster and penetrates deeper into the gastrointestinal wall, resulting in higher levels of the TNFα antibody or functional fragment thereof. Finally, it has been found that the TNFα antibody or functional fragment thereof taken up by the large intestinal wall is retained there effectively.

The present invention provides a composition for use in the topical treatment of inflammatory bowel diseases. The present invention therefore relates to the subject matter defined in the following items 1 to 64.

1. A composition comprising an active agent for use in the topical treatment of an inflammatory bowel disease, wherein said treatment results in a decrease of a pH in the large intestinal lumen of a human patient, and wherein said active agent is
(i) an antibody specific to an antigen selected from the group consisting of tumor necrosis factor alpha (TNFα); anti-inflammatory cytokines such as IL-13 as well as their receptors; pro-inflammatory cytokines, such as IL-6, IL-12 and IL-23 (IL-12/IL-23p40, IL-23p19), IL-17, IL-21 as well as their receptors; cell adhesion molecules, such as MadCAM-1, ICAM-1; C-C chemokine receptors, such as CCR5, CCR9 and their ligands; integrins, such as alpha4beta7, beta7, alpha2beta1, alphaEbeta7; toll-like receptors, such as TLR2, TLR9; eotaxins, such as Eotaxin-1; members of the tumor necrosis factor receptor superfamily, such as OX40; matrix metalloproteinases, such as MMP-9; C-X-C motif chemokines, such as IP-10; and other proteins, such as CD20;
or
(ii) a functional fragment of said antibody.

2. The composition for use according to item 1, wherein said composition reduces the pH of a local microenvironment of the antibody or functional fragment thereof in the large intestinal lumen.

3. The composition for use according to items 1 or 2, wherein said treatment results in a decrease of a pH in the colonic lumen of a human patient suffering from an inflammatory bowel disease.

4. The composition for use according to items 1 to 3, wherein said treatment results in a decrease of a pH in the lumen of the terminal ileum of a human patient suffering from an inflammatory bowel disease.

5. The composition for use according to any one of the items above, wherein the human patient is a patient suffering from Crohn's disease or ulcerative colitis.

6. The composition for use according any one of the items above, wherein the human patient is in remission, or suffers from a mild or moderate form of the inflammatory bowel disease.

7. The composition for use according to any one of the items above, wherein the decrease of pH in the large intestinal lumen facilitates the uptake and/or penetration of the active agent into the gastrointestinal wall.

8. The composition for use according to any of the above items, wherein said treatment results in a pH in the large intestinal lumen below 7.

9. The composition for use according to any of the above items, wherein said treatment results in a pH in the large intestinal lumen below 6.5.

10. The composition for use according to any of the above items, wherein said treatment results in a pH in the large intestinal lumen below 6.3, preferably around 6.

11. The composition for use according to any of the above items, wherein said treatment results in a pH in the large intestinal lumen below 6.1.

12. The composition for use according to any of items 1 to 8, wherein said treatment results in a pH in the large intestinal lumen, preferably the colonic lumen, from 5.5 to 6.5, preferably from 5.6 to 6.4, more preferably from 5.7 to 6.3, even more preferably from 5.8 to 6.2, most preferably from 5.9 to 6.1, e.g. about 6.0.

13. The composition for use according to any one of items 1 to 8, wherein said treatment results in a pH in the terminal ileum below 7, preferably below 6.5, more preferably below 6.3, even more preferably around 6.

14. The composition for use according to any of the above items, comprising at least one additive selected from the group consisting of acidifiers, buffer agents, and combinations thereof.

15. The composition for use according to item 14, wherein (i) the at least one additive is an acidifier selected from the group consisting of acetic acid, adipic acid, ascorbic acid, citric acid, fumaric acid, itaconic acid, lactic acid, maleic acid, malic acid, phosphoric acid, propionic acid, sorbic acid, succinic acid and tartaric acid; and/or wherein (ii) the at least one additive is a buffer agent selected from the group consisting of Tris-citrate buffer (Tris+citric acid+sodium citrate), citrate buffer (citric acid+sodium citrate), phosphate citrate buffer (dibasic sodium phosphate+citric acid), phosphate buffer (sodium phosphate monobasic+sodium phosphate dibasic).

16. The composition for use according to any of items 1 to 5 and 7 to 15, wherein said treatment results in a decrease of the pH in the large intestinal lumen of a human patient suffering from an inflammatory bowel disease with active disease.

17. The composition for use according any one of the items above, wherein the composition provides a therapeutically effective dose of the antibody or functional fragment thereof in the large intestinal lumen of a human patient.

18. The composition for use according any one of the items above, wherein the composition provides a concentration of the antibody or functional fragment thereof in the large intestinal lumen of a human patient in the range of 0.02 to 2 mg/ml, preferably 0.2 to 1 mg/ml.

19. The composition for use according to any one of items 17-18, wherein said treatment further provides a concentration of the antibody or functional fragment thereof in the range of 0.02 to 1 mg/ml, preferably 0.2 to 0.8 mg/ml.

20. The composition for use according item 18, wherein the composition provides a concentration of the antibody or functional fragment thereof in the colonic lumen of a human patient in the range of 0.02 to 2 mg/ml, preferably 0.2 to 1 mg/ml.

21. The composition for use according item 18, wherein the composition provides a concentration of the antibody or functional fragment thereof in the lumen of the terminal ileum of a human patient in the range of 0.02 to 2 mg/ml, preferably 0.2 to 1 mg/ml.

22. The composition for use according to items 17 to 21, wherein the concentration of the antibody or functional fragment thereof is in the range of 0.02 to 0.4 mg/ml, preferably around 0.2 mg/ml, and wherein the antibody or functional fragment thereof effectively penetrates at least part, and preferably the entire depth, of the gastrointestinal wall.

23. The composition for use according to item 22, wherein the concentration of the antibody or functional fragment thereof is in the range of 0.05 mg/ml to 0.35 mg/ml, preferably 0.1 mg/ml to 0.3 mg/ml, more preferably 0.15 mg/ml to 0.25 mg/ml, most preferably around 0.2 mg/ml.

24. The composition for use according to any of items 18 to 21, wherein the concentration of the antibody or the functional fragment thereof is in the range of 0.4 to 1 mg/ml.

25. The composition for use according to item 24, wherein the concentration of the antibody or functional fragment thereof in the large intestinal lumen is in the range of 0.5 mg/ml to 0.95 mg/ml, preferably 0.6 mg/ml to 0.9 mg/ml, more preferably 0.75 mg/ml to 0.85 mg/ml, most preferably around 0.8 mg/ml.

26. The composition for use according to any one of items 1 to 17, further providing a high concentration of antibody or functional fragment thereof in the large intestinal lumen, for human patients with high levels of gastrointestinal inflammation.

27. The composition for use according to item 26, wherein the high concentration of antibody or functional fragment thereof in the large intestinal lumen is 0.8 mg/ml or higher.

28. The composition for use according to items 1 to 17, further providing a concentration of antibody or functional fragment thereof in the large intestinal lumen of about 0.2 mg/ml, for human patients with low to moderate levels of gastrointestinal inflammation.

29. The composition for use according to any one of the preceding items, wherein the functional antibody fragment is a Fab fragment, a F(ab')2 fragment, a Fab' fragment, an scFv, a dsFv, a VHH, a diabody, a triabody, a tetrabody, an Fc fusion protein or a minibody.

30. The composition for use according to any one of the above items, wherein the composition is a solid dosage form.

31. The composition for use according to item 30, wherein the solid dosage form is in the form of a pellet/pellets, granule/granules, micro particle/micro particles, nano particle/nano particles, mini tablet/mini tablets, capsule or tablet.

32. The composition for use according to items 30 or 31, wherein the solid dosage form comprises at least one additive as defined in item 14 or 15, which preferably is in a matrix with the antibody or functional fragment thereof, and which is part of a layer or compartment.

33. The composition for use according to item 32, wherein said at least one additive is part of a layer.

34. The composition for use according to item 33, wherein said at least one additive is part of a layer not containing the active agent.

35. The composition for use according to item 34, wherein the layer comprising the at least one additive is applied onto the core of the solid dosage form comprising the antibody or functional fragment thereof.

36. The composition for use according to item 32, wherein said at least one additive is part of a compartment or layer separate from a compartment or layer comprising the antibodies or functional fragments thereof, and wherein the compartment or layer comprising the at least one additive comprises 1-80%, preferably 2-65%, more preferably 5-50%, even more preferably 10-40% additive, relative to the total weight of the dry compartment or layer.

37. The composition for use according to item 32 or 36, wherein the compartment or layer comprising the at least one additive further comprises hydrophilic polymers, fillers, disintegrants, anti-tacking agents and/or lubricants.

38. The composition for use according to any one of the preceding items, wherein said treatment comprises the oral administration of the composition.

39. The composition for use according to item 38, wherein the composition is a solid dosage form in the form of a pellet, granule, micro particle, nano particle, mini tablet, capsule or tablet, preferably a pellet or tablet, coated with a coating material that prevents release of the active agent before the ileocolonic region of the intestine.

40. The composition according to item 39, wherein the coating material is selected from the group consisting of materials that disintegrate pH-dependently, materials that disintegrate time-dependently, materials that disintegrate due to enzymatic triggers in the large intestinal environment, and combinations thereof.

41. The composition for use according to item 40, wherein the coating material is selected from the group comprising Poly vinyl acetate phthalate, Cellulose acetate trimellitate, Hydroxypropyl methylcellulose phthalate HP-50, Hydroxypropyl methylcellulose phthalate HP-55, Hydroxypropyl methylcellulose phthalate HP-55S, Hydroxypropyl methylcellulose acetate succinate, Cellulose acetate phthalate, Acrylic acid copolymer, Eudragit L100-55, Eudragit L30D-55, Eudragit L-100, Eudragit L12.5, Eudragit S-100, Eudragit S12,5, Eudragit FS30D, Hydroxyl propylethyl cellolose phthalate, PEG 6000, Ac-di-sol, Talc, Hydroxy propyl methyl cellulose acetate succinate (HPMCAS), Hydroxy ethyl cellulose, ethylcellulose, microcrystalline cellulose, Hydroxy propyl methyl cellulose, Chondroitin sulphate, Pectin, Guar gum, Chitosan, Lactose, Maltose, Cellobiose, Inulin, Cyclodextrin, Lactulose, Raffinose, Stachyose, Alginate, Dextran, Xantham gum, Guar gum, Starch, Tragacanth, Locust bean gum, Cellulose, Arabinogalactan, Amylase, or a combination thereof.

42. The composition for use according to any one of items 1 to 37, wherein said treatment comprises the rectal administration of the composition, and/or wherein the composition is an enema, a gel, a foam or a suppository.

43. The composition for use according to any one of the preceding items, wherein the pH in the large intestinal lumen of the human patient before the treatment is higher than 6.5, preferably higher than 6.7, more preferably higher than 6.9.

44. The composition for use according to any one of the items above, further providing a concentration of the antibody or functional fragment thereof in the large intestinal lumen, which directly correlates with tissue levels of the antibody or functional fragment thereof which are taken up into the gastrointestinal wall at the site of said concentration.

45. The composition for use according to any one of the items above, wherein the topical treatment results in an increased uptake of the antibody or functional fragment thereof into the gastrointestinal wall at sites of inflammation.

46. The composition for use according to any one of the items above, wherein the topical treatment results in a faster uptake of the antibody or functional fragment thereof into the gastrointestinal wall at sites of inflammation.

47. The composition for use according to any one of the items above, wherein the topical treatment results in a faster penetration of the antibody or functional fragment thereof into the deeper submucosal layer of the gastrointestinal wall at sites of inflammation.

48. The composition for use according to any one of the items above, wherein the topical treatment results in a retention of antibody or functional fragment thereof in the gastrointestinal wall, without major systemic release into the rest of the body.

49. The composition for use according to any one of the items above, wherein said use provides a concentration of antibody or functional fragment thereof in the large intestinal lumen effective in the topical treatment inflammatory bowel diseases in a human patient with enhanced absorption capacity for the antibodies specific to antibodies or a functional fragments thereof at sites of partially impaired integrity of the gastrointestinal wall.

50. The composition for use according to any one of the preceding items, wherein the antibody or functional fragment thereof is an anti-TNFα antibody.

51. The composition for use according to item 50, wherein the anti-TNFα antibody or functional fragment thereof is infliximab.

52. The composition for use according to item 50, wherein the anti-TNFα antibody or functional fragment thereof is adalimumab.

53. The composition for use according to any one of items 1 to 49, wherein the antibody or functional fragment thereof is a functional fragment of an anti-TNFα antibody.

54. The composition for use according to item 53, wherein the functional fragment of an anti-TNFα antibody is a Fab fragment.

55. The composition for use according to item 54, wherein the functional fragment of an anti-TNFα antibody is a Fab fragment of infliximab.

56. The composition for use according to item 54, wherein the functional fragment of an anti-TNFα antibody is a Fab fragment of adalimumab.

57. The composition for use according to items 1 to 49, wherein the antibody or functional fragment thereof is selected from infliximab, adalimumab, Fab fragment of infliximab and Fab fragment adalimumab.

58. A process for manufacturing the composition as defined in any one of items 1 to 57, comprising
 a) providing an antibody or a functional fragment thereof,
 b) at least one additive, and
 c) coating components a) and b) with a coating material that enables the application according to items 38 to 42.

59. The process according to item 58, wherein the additives comprise at least one buffer agent and/or acidifier.

60. The process according to item 59, wherein the at least one acidifier is selected from the group consisting of acetic acid, adipic acid, ascorbic acid, citric acid, fumaric acid, itaconic acid, lactic acid, maleic acid, malic acid, phosphoric acid, propionic acid, succinic acid, sorbic acid and tartaric acid.

61. The process according to item 59, wherein the at least one buffer agent is selected from the group consisting of Tris-citrate buffer (Tris+citric acid+sodium citrate), citrate buffer (citric acid+sodium citrate), phosphate citrate buffer (dibasic sodium phosphate+citric acid), phosphate buffer (sodium phosphate monobasic+sodium phosphate dibasic).

62. The composition for use according to any one of items 1 to 57, wherein the antibody or functional fragment thereof is selected from the group consisting of antibodies specific to TNFα and functional fragments thereof.

63. The composition for use according to any one of items 1 to 57 and 62, wherein said treatment comprises administering the antibody or functional fragment thereof once per day, twice per day, or three times per day to the human patient.

64. The composition for use according to item 63, wherein said treatment comprises administering the antibody or functional fragment thereof once per day to the human patient.

DETAILED DESCRIPTION

Figure 1:
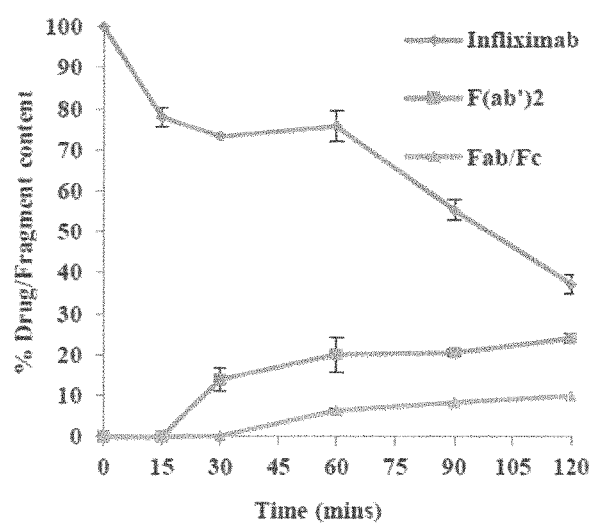
FIG. 1: Stability of A) infliximab, B) adalimumab in Human colonic model fecal inoculum, and C) SDS-PAGE gel confirming the conversion of adalimumab to F(ab')2, Fab and Fc fragments, detected by silver staining at 1 h incubation time point. The fragmentation of infliximab was confirmed similarly by SEC and SDS-PAGE (Data not shown). Each value represents mean±S.D (n=3). Lane 1, protein molecular weight standard; Lane 2, intact mAb adalimumab detected in the colonic model at 1 h; Lane 3, adalimumab F(ab')2 formation detected in the colonic model at 1 h; Lane 4, adalimumab Fc and Fab formation detected in the colonic model at 1 h.
Figure 1:
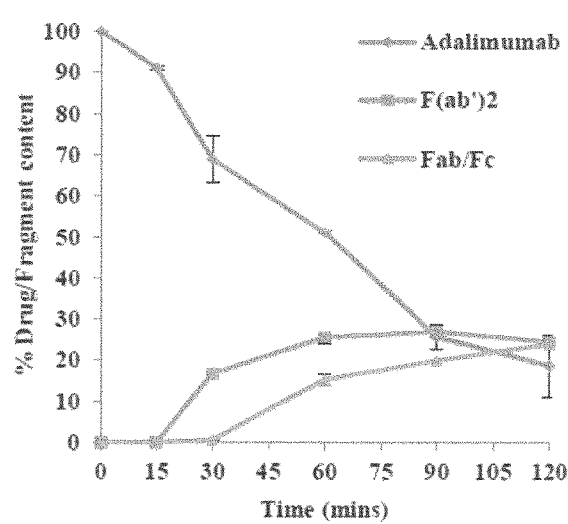
Figure 1:
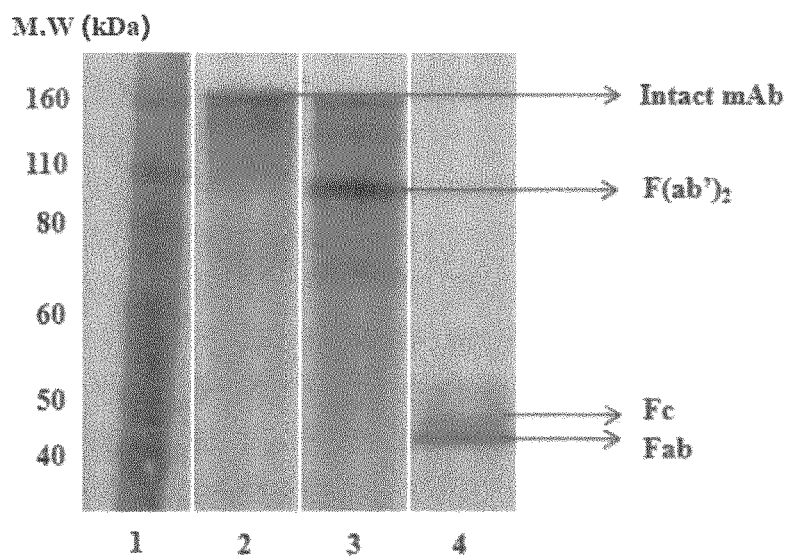

The present invention is described in the following with regard to antibodies specific to tumor necrosis factor alpha (TNFα) and functional fragments thereof, which represent the most preferred embodiments. All embodiments described hereinafter equally apply to antibodies and functional fragments thereof directed to other targets (antigens) mutatis mutandis. The targets of these antibodies and functional fragments thereof include, but are not limited to, anti-inflammatory cytokines such as IL-13 as well as their receptors; pro-inflammatory cytokines, such as IL-6, IL-12 and IL-23 (IL-12/IL-23p40, IL-23p19), IL-17, IL-21 as well as their receptors; cell adhesion molecules, such as MadCAM-1, ICAM-1; C-C chemokine receptors, such as CCR5, CCR9 and their ligands; integrins, such as alpha4beta7, beta7, alpha2beta1, alphaEbeta7; toll-like receptors, such as TLR2, TLR9; eotaxins, such as Eotaxin-1; members of the tumor necrosis factor receptor superfamily, such as OX40; matrix metalloproteinases, such as MMP-9; C-X-C motif chemokines, such as IP-10; and other proteins, such as CD20. Preferred targets are α4β7 integrin and CD20.

The present invention relates to a composition comprising an active agent selected from the group consisting of antibodies specific to tumor necrosis factor alpha (TNFα) and functional fragments thereof, for use in the topical treatment of an inflammatory bowel disease, wherein said treatment results in a decrease of a pH in the large intestinal lumen of a human patient.

In the context of the present application, the term "antibody" is used as a synonym for "immunoglobulin" (Ig), which is defined as a protein belonging to the class IgG, IgM, IgE, IgA, or IgD (or any subclass thereof), and includes all conventionally known antibodies and functional fragments thereof. In the context of the present invention, a "functional fragment" of an antibody/immunoglobulin is defined as antigen-binding fragment or other derivative of a parental antibody that essentially maintains the properties of such a parental antibody.

An "antigen-binding fragment" of an antibody/immunoglobulin is defined as a fragment (e.g., a variable region of an IgG) that retains the antigen-binding region. An "antigen-binding region" of an antibody typically is found in one or more hypervariable region(s) of an antibody, i.e., the CDR-1, -2, and/or -3 regions. "Antigen-binding fragments" of the invention include the domain of a F(ab')$_2$ fragment and a Fab fragment. "Functional fragments" of the invention include Fab fragment, F(ab')$_2$ fragment, Fab' fragment, scFv, dsFv, VHH, diabody, triabody, tetrabody, Fc fusion protein and minibody. The F(ab')$_2$ or Fab domain may be engineered to minimize or completely remove the intermolecular disulphide interactions that occur between the CH1 and CL domains. The antibodies or functional fragments of the present invention may be part of bi- or multifunctional constructs.

Preferred functional fragments of the present invention are Fab fragments, F(ab')$_2$ fragments, Fab' fragments, scFv and diabodies.

Fab fragments can be obtained as the purified digestion products after digestion of a TNFα-specific antibody with a cysteine proteinase like papain (EC 3.4.22.2). F(ab')$_2$ fragments can be obtained as the purified digestion products after digestion of a TNFα-specific antibody with pepsin (EC 3.4.23.1) or IdeS (Immunoglobulin degrading enzyme from *Streptococcus pyogenes*; EC 3.4.22). Fab' fragments can be obtained from F(ab')$_2$ fragments in mild reducing conditions, whereby each F(ab')$_2$ molecule gives rise to two Fab' fragments.

An scFv is a single chain Fv fragment in which the variable light ("$V_L$") and variable heavy ("$V_H$") domains are linked by a peptide bridge.

A "diabody" is a dimer consisting of two fragments, each having variable regions joined together via a linker or the like (hereinafter referred to as diabody-forming fragments), and typically contain two $V_L$s and two $V_H$s. Diabody-forming fragments include those consisting of $V_L$ and $V_H$, $V_L$ and $V_L$, $V_H$ and $V_H$, etc., preferably $V_H$ and $V_L$. In diabody-forming fragments, the linker joining variable regions is not specifically limited, but preferably short enough to avoid noncovalent bonds between variable regions in the same fragment. The length of such a linker can be determined as appropriate by those skilled in the art, but typically 2-14 amino acids, preferably 3-9 amino acids, especially 4-6 amino acids are used. In this case, the $V_1$ and $V_H$ encoded on the same fragment are joined via a linker short enough to avoid noncovalent bonds between the $V_1$ and $V_H$ on the same chain and to avoid the formation of single-chain variable region fragments so that dimers with another fragment can be formed. The dimers can be formed via either covalent or noncovalent bonds or both between diabody-forming fragments.

Moreover, diabody-forming fragments can be joined via a linker or the like to form single-chain diabodies (sc(Fv)$_2$). By joining diabody-forming fragments using a long linker of about 15-20 amino acids, noncovalent bonds can be formed between diabody-forming fragments existing on the same chain to form dimers. Based on the same principle as for preparing diabodies, polymerized antibodies such as trimers or tetramers can also be prepared by joining three or more diabody-forming fragments.

Preferably, the antibody or functional fragment of the invention specifically binds to TNFα. The terms "anti-TNFα antibody", "TNFα antibody" and "antibody specific to TNFα" as used herein are interchangeable. In its most general form (and when no defined reference is mentioned), "specific binding" refers to the ability of the antibody or functional fragment to discriminate between human TNFα and an unrelated biomolecule, as determined, for example, in accordance with a specificity assay methods known in the art. Such methods comprise, but are not limited to, Western blots and enzyme-linked immunosorbent assay (ELISA) tests. For example, a standard ELISA assay can be carried out. Typically, determination of binding specificity is performed by using not a single reference biomolecule, but a set of about three to five unrelated biomolecules, such as milk powder, BSA, transferrin or the like. In one embodiment, specific binding refers to the ability of the antibody or fragment to discriminate between human TNFα and human TNFβ. In a preferred embodiment of the present invention the TNFα antibody or functional fragment thereof is a TNFα antibody. In an alternatively preferred embodiment of the present invention the TNFα antibody or functional fragment thereof is a functional fragment of a TNFα antibody.

The term "topical treatment" in the context of the present application, is used to describe the local application of the composition, as opposed to the systemic application of TNFα antibody containing composition, e.g. by intravenous infusion or subcutaneous injection, used in commercial products. However, the topical treatment in the intestinal lumen is not limited by the way of administration of the composition. The term "administration" in this context relates to the manner and form in which the composition comes into first contact with the body of a patient. This means that the composition in a suitable form can be administered orally, rectally or in any other way that results in the accumulation of the composition at the site of local application.

In the present invention the term "large intestinal lumen" is used for the combined and continuous inside of the large intestine and the terminal ileum of the small intestine. The large intestine is the penultimate section of the gastrointestinal tract and can be further subdivided into cecum, colon and rectum. The colon can be further subdivided into ascending, transverse and descending colon. The terminal ileum of the small intestine is the penultimate section of the small intestine and is directly adjacent to the cecum. In one embodiment, the term "large intestinal lumen" refers to the continuous inside of the large intestine. The term "gastrointestinal tract" as used herein describes the system of organs of the human body, that includes all structures between mouth and anus, forming a continuous passage, and is responsible for digesting ingested material, absorbing nutrients and expelling faeces.

The topical treatment with the composition of the present invention results in a decrease of a pH in the large intestinal lumen of a human patient. Surprisingly, it has been found by the present inventors that the uptake and penetration of anti-TNFα antibodies into the large intestinal wall is particularly effective if the pH in the colon is weakly acidic. In particular, it has been found that the uptake and penetration into the large intestinal wall is more effective at a weakly acidic pH, e.g. a pH of 6, than at a neutral or weakly basic pH, e.g. a pH of 7.4. Therefore, in one embodiment of the present invention the decrease of pH in the large intestinal lumen facilitates the uptake and/or penetration of the active agent into the gastrointestinal wall.

In the present invention the term "large intestinal wall" is used to define the multilayered tissue that surrounds the large intestinal lumen and forms a barrier between the large intestinal lumen and the rest of the body. In the context of the present invention, in its broadest definition the large intestinal wall also includes the gastrointestinal wall of the terminal ileum. This barrier allows for the active and passive absorption of a defined set of nutrients and other molecules, including antibodies and fragments thereof. The large intestinal wall is built of several layers. These include, starting with the layer facing the large intestinal lumen, a mucosal layer or mucosa followed by a submucosal layer or submucosa. The mucosa can be further subdivided, starting from the lumen facing side, into an epithelium, a lamina propria and a muscularis mucosa. At the luminal side, the mucosal layer is protected by a "mucus layer", which is a viscous proteinous gel with glycoproteins of the mucin family as main components. The large intestinal wall is part of the gastrointestinal wall. The gastrointestinal wall corresponds to the tissue that surrounds the gastrointestinal tract and forms a barrier between the gastrointestinal tract and the rest of the body.

The term "uptake" as used herein in its broadest definition refers to the absorption of molecules, like antibodies or functional fragments thereof, into the gastrointestinal wall. In a more specific definition, uptake may refer to the fraction of the total dose of anti-TNFα antibodies or functional fragments thereof in the large intestinal lumen, or in a subvolume of the large intestinal lumen, that transfers into the large intestinal wall, or may refer to the amount of anti-TNFα antibodies or functional fragments thereof that transfers into a defined amount of large intestinal wall tissue. The term "penetration" as used herein may refer to the depth to which the anti-TNFα antibodies or functional fragments thereof pass into the large intestinal wall. In accordance with this definition, the submucosal layer is located deeper within the large intestinal wall than the mucosal layer.

In the prior art, pH values in the human colon have been reported in the range of 6.5 to 7.5. The in vivo surface pH of the human colonic mucosa has been reported to range between pH 7.1 and 7.5 and to be consistently higher at all anatomical segments than luminal pH (McDougall et al., Dig. Dis. Sci. 1993; 38:542-5). In light of this, in accordance with the above findings of the present inventors, decreasing the pH in the large intestinal lumen at the site where the anti-TNFα antibodies or functional fragments thereof are released from the composition, it is important to ensure optimal uptake and penetration of the anti-TNFα antibodies or functional fragments thereof into the large intestinal wall. Therefore, the composition of the present invention is provided in a form that results in a decrease of a pH in the large intestinal lumen of a human patient during treatment with the anti-TNFα antibody or functional fragment thereof. This decrease of a pH is understood to refer to a decrease in at least part of the large intestinal lumen, for example in a section or subvolume of the large intestinal lumen, or in the local microenvironment of the anti-TNFα antibody or functional fragment thereof released from the composition. Moreover, in one embodiment this decrease of a pH in the large intestinal lumen, is understood to preferably refer to a decrease at or close to the gastrointestinal wall on the luminal side (as opposed to the serosal side of the gastrointestinal wall) rather than to a general decrease in the lumen itself. In an alternative embodiment of the present invention, the treatment with the composition of the present invention results in a decrease of a pH in the colonic lumen of a human patient. In another alternative embodiment, the treatment with the composition of the present invention results in a decrease of a pH in the lumen of the ascending colon of a human patient. In yet another alternative embodiment, the treatment with the composition of the present invention results in a decrease of a pH in the lumen of the transverse colon of a human patient. In a further alternative embodiment, the treatment with the composition of the present invention results in a decrease of a pH in the lumen of the descending colon of a human patient. In a further alternative embodiment, the treatment with the composition of the present invention results in a decrease of a pH in the lumen of the proximal colon of a human patient. In a further alternative embodiment, the treatment with the composition of the present invention results in a decrease of a pH in the lumen of the distal colon of a human patient.

Means to measure the pH in the large intestinal lumen are known in the art. The pH in the large intestinal lumen can for example be measured using a radiotelemetry capsule, e.g. a wireless motility capsule (WMC), a pH sensitive electrode passed orally, or the IntelliCap® system (Medimetrics).

In one embodiment of the present invention, the composition is capable of reducing the pH of a local microenvironment of the antibody or functional fragment in the large intestinal lumen. Microenvironments are spaces, wherein specific conditions are controlled and maintained in order to obtain specific therapeutic effects, i.e. by delivering a tailored medicament composition into a target area of a living body for a therapeutic effect. In one embodiment, the term "microenvironment" as used herein refers to the site or subvolume in the large intestinal lumen, which is characterized by a decreased pH to promote the controlled release of the anti-TNFα antibody or fragment thereof from the composition. In another embodiment, the local microenvironment of the antibody or functional fragment thereof, refers to the site or subvolume in the intestinal lumen, where the antibodies or functional fragments thereof are released from the composition.

According to one embodiment of the present invention, the topical treatment with the composition results in a pH in the large intestinal lumen below 7, preferably below 6.5, more preferably below 6.3, even more preferably around 6. In another embodiment, the topical treatment result in a pH in the large intestinal lumen, preferably the colonic lumen, from 5.5 to 6.5, preferably from 5.6 to 6.4, more preferably from 5.7 to 6.3, even more preferably from 5.8 to 6.2, most preferably from 5.9 to 6.1, e.g. about 6.0. The term "results in a pH in the large intestinal lumen below" followed by a specific value, e.g. 7, 6.5, etc., is not to be understood to mean that the treatment results in a luminal pH below said value throughout the whole of the large intestinal lumen, but means that it results in a luminal pH in part of the large intestinal lumen, for example in a section or subvolume of the large intestinal lumen or in the local microenvironment of the anti-TNFα antibodies or functional fragments thereof released from the composition.

Suitable means to reduce the pH e.g. in the large intestinal lumen are known in the art. Suitable means to reduce the luminal pH to be within a desired range include e.g. buffer agents and/or acidifiers. The term "acidifier" as used herein refers to a substance or agent that directly or indirectly causes acidification. An acidifier for example is an organic or inorganic substance that either is, becomes or produces acids. In a preferred embodiment of the present invention the composition comprises as an additive at least one buffer agent and/or acidifier. Acidifiers suitable for human ingestion are known in the art. Examples of suitable acidifiers for the composition of the present invention are acetic acid, adipic acid, ascorbic acid, citric acid, fumaric acid, itaconic acid, lactic acid, maleic acid, malic acid, phosphoric acid, propionic acid, sorbic acid, succinic acid and tartaric acid. Examples of suitable buffer agents include, but are not limited to, Tris-citrate buffer (Tris+citric acid+sodium citrate), citrate buffer (citric acid+sodium citrate), phosphate citrate buffer (dibasic sodium phosphate+citric acid), phosphate buffer (sodium phosphate monobasic+sodium phosphate dibasic).

According to the present invention, the composition may be in any form that upon administration allows topical treatment in the large intestinal lumen of a human patient. The composition may be a solid dosage form in the form of pellets, granules, micro particles, nano particles, mini tablets, capsules or tablets and the like. It is known in the art how to manufacture solid dosage forms, for example it can be referred to "Aulton's Pharmaceutics: The Design and Manufacture of Medicines", Churchill Livingstone title, 4th revised edition, 2013 (ISBN: 978-0-7020-4290-4). If the inventive composition comprises at least one additive selected from buffer agents, acidifiers and combinations thereof, the anti-TNFα antibody or functional fragment thereof and the at least one additive may be part of the same compartment or layer of the solid dosage form, or may be part of separate compartments or layers. In one embodiment of the present invention the additive is part of a compartment or layer and is in a matrix with the anti-TNFα antibody or functional fragment thereof. A "compartment" of a solid dosage form as used herein is a section of whole solid dosage form that forms a distinct subunit of the solid dosage form, separable from neighboring compartments of the solid dosage form by its physicochemical properties. Compartments may be in the form of granules, particles, micro particles, nano particles, pellets, mini capsules or mini tablets and the like, which are combined into the solid dosage form. A "layer" of a solid dosage form as used herein is e.g. a film or coating of defined thickness, which is applied to an inert core or to a another layer already applied to an inert core, and which is separable from the core of the solid dosage form or other layers by its physicochemical properties. How to apply a layer to an inert core or on top of another layer is known in the art. Depending on the constituents of the inert core and the one or more layers of the solid dosage form, upon exposure to aqueous medium the different layers may dissolve sequentially, with the outermost layer first, followed by the layer just underneath etc.; partially sequentially with outermost starting first but the layer underneath starting to dissolve before the outermost layer is fully dissolved; or essentially simultaneously, optionally supported by the swift disintegration of the inert core, e.g. due to the presence of disintegrants.

If the anti-TNFα antibody or functional fragment thereof and the at least one additive selected from buffer agents, acidifiers and combinations thereof are part of different compartments of the solid dosage form, they may be released simultaneously or sequentially, preferably simultaneously, in analogy to the release of different layers as described above. If the anti-TNFα antibody or functional fragment thereof and the at least one additive are part of different compartments and are released sequentially or partially sequentially, the at least one additive is preferably released first.

If the anti-TNFα antibody or functional fragment thereof and the at least one additive are part of different layers of the solid dosage form, the layers may be separated by one or more intermediate layers. If the anti-TNFα antibody or functional fragment thereof and the at least one additive are part of different layers and are released sequentially or partially sequentially, the at least one additive is preferably released first.

The core, layers and/or compartments of the solid dosage form may comprise further additives, like hydrophilic binders, fillers, disintegrants, plasticizers, anti-tacking agents and lubricants. Suitable hydrophilic binders, filler, disintegrants, plasticizers, anti-tacking agents and lubricants are known to those of skill in the art. Examples of hydrophilic binders include copovidone, hydroxypropylmethylcellulose, polyvinylpyrrolidone and hydroxypropylcellulose. Examples of fillers include lactose, maltodextrin, mannitol, microcrystalline cellulose, pregelatinized starch and sucrose esters. Examples of disintegrants include crospovidone, croscarmellose sodium, sodium starch glycolate, microcrystalline cellulose, and pregelatinized starch. Examples of anti-tacking agents include colloidal silicon dioxide, talc, magnesium stearate, glyceryl monostearate. Examples of lubricants include magnesium stearate, calcium stearate, glyceryl monostearate, hydrogenated castor oil, sodium lauryl sulfate, sodium stearyl fumarate, stearic acid, zinc stearate, talc, and sucrose esters.

In one embodiment of the present invention, the composition in the form of a solid dosage form is comprising from about 0.1 to about 50% by weight, based on the total dosage form (preferably from about 1 to about 30% by weight based on the total dosage form), of an anti-TNFα antibody or functional fragment thereof or a combination of anti-TNFα antibodies and/or functional fragments thereof; from about 1 to about 60% by weight, based on the total dosage form (preferably from about 5 to about 50% by weight based on the total dosage form), of at least one additive selected from buffer agents, acidifiers and combinations thereof; and from about 0 to about 95% by weight of the total dosage form of other additives.

In one embodiment where the at least one additive selected from buffer agents, acidifiers and combinations thereof in the solid dosage form is part of a compartment or layer separate from the compartment or layer comprising the anti-TNFα antibody or functional fragment thereof, the compartment or layer comprising the at least one additive may comprise 1-80%, preferably 2-65%, more preferably 5-50%, even more preferably 10-40% additive, relative to the total weight of the compartment or layer, and may further comprise hydrophilic polymers, fillers, disintegrants, anti-tacking agents and lubricants.

In accordance with the present invention, the concentration in the large intestinal lumen of the TNFα antibody or functional fragment thereof upon administration of the inventive composition is not particularly limited. In one embodiment of the present invention the concentration of the anti-TNFα antibody or functional fragment thereof in the large intestinal lumen upon administration of the inventive composition is in the range of 0.02 mg/ml to 2 mg/ml, preferably 0.2 mg/ml to 1 mg/ml, more preferably 0.2 mg/ml to 0.8 mg/ml.

The present inventors have found that by increasing the concentration of the anti-TNFα antibody or functional fragment thereof at the luminal side of the large intestinal wall, for example from 0.02 mg/ml step-wise to 2 mg/ml, also the antibody uptake into the gastrointestinal wall in a given amount of time increases. Therefore, in one embodiment of the present invention the composition for use in the topical treatment in the large intestinal lumen of a human patient, provides a concentration of the anti-TNFα antibody or functional fragment thereof in the large intestinal lumen, which directly correlates with the tissue level of the anti-TNFα antibody or functional fragment thereof taken up into the large intestinal wall. The level/extent of gastrointestinal inflammation due to the inflammatory bowel disease may vary between patients as well as for a given patient at different times. How to determine the level/extent of gastrointestinal inflammation due to the inflammatory bowel disease is known in the art. The level/extent of gastrointestinal inflammation due to the inflammatory bowel disease can for example be determined by measuring the level of a faecal or serologic biomarker of gastrointestinal inflammation in stool or blood samples, respectively, of a patient, preferably a faecal biomarker. Faecal biomarkers of gastrointestinal inflammation include calprotectin, lactoferrin, S100A12 or TNFα and can be determined by using immunochemical techniques.

In accordance with the above finding, the dose of anti-TNFα antibody or functional fragment thereof provided to a patient may be adapted to the individual needs of each patient. Therefore, in another embodiment of the present invention, the composition further provides a concentration of the anti-TNFα antibody or functional fragment thereof, in the large intestinal lumen that is adaptable to the level of inflammation in the large intestine of the human patient, such that a patient with a high level of gastrointestinal inflammation in the large intestine is provided with a higher concentration of anti-TNFα antibody or functional fragment thereof in the large intestinal lumen, resulting in a higher level of anti-TNFα antibody or functional fragment thereof taken up by the targeted large intestinal wall, than a patient with a lower level of inflammation.

Moreover, the present inventors found that already a relatively low concentration of anti-TNFα antibody or functional fragment thereof at the luminal side of the large intestinal wall, e.g. of about 0.2 mg/ml, is taken up quickly and efficiently into the large intestinal wall and effectively penetrates deep into the submucosal layer within 2 h of the first exposure. Therefore, in a further embodiment of the present invention the composition provides a concentration of anti-TNFα antibody or functional fragment thereof in the large intestinal lumen of about 0.2 mg/ml, for human patients with low to moderate levels of gastrointestinal inflammation. Patients may have low to moderate levels of gastrointestinal inflammation, due to a less severe form of the inflammatory bowel disease (i.e. a mild or moderate form of the inflammatory bowel disease), or due to the fact that they are in remission.

Concentrations within the above ranges in the large intestinal lumen can be achieved by means of targeted accumulation of anti-TNFα antibodies or functional fragments thereof. The way and means of targeted accumulation in the large intestinal lumen are not particularly limited and can be achieved by methods known in the art. These include taking advantage of the innate processes of the gastrointestinal tract that result e.g. in differences in pH and microflora and specific residence times of ingested materials in different sections of the gastrointestinal tract. Methods for sampling concentrations of specific proteins including specific antibodies in the large intestinal lumen are known in the art. Samples can be collected for example from expelled faeces, or using a flexible tube inserted via the anus into the large intestine. TNFα antibody concentration can then be determined using ELISA or Western Blots or other immunochemical techniques, similarly to what has been described for the measurement of faecal TNFα concentration in Nicholls et al. (J Clin Pathol. 1993 August; 46(8): 757-760), with an antibody specific to the anti-TNF antibody or functional fragment thereof used in the composition.

It has been found that, if the mucus layer of the large intestinal wall is impaired, uptake of anti-TNFα antibodies or functional fragments thereof into the large intestinal wall is markedly increased. Moreover, if the mucus layer of the large intestinal wall is impaired, anti-TNFα antibodies or functional fragments thereof are taken up faster; such that e.g. already 30 min after initial exposure to anti-TNFα antibodies or functional fragments thereof, significantly more anti-TNFα antibodies or functional fragments thereof can be found in the colonic mucosa, if the mucus layer is impaired. Finally, in case of impairment of the mucus layer, this results in fast penetration of a considerable fraction, of the anti-TNFα antibodies or functional fragments thereof taken up, deep into the submucosal layer.

Impairment of the intestinal mucus layer is considered a characteristic feature of IBD and is thought to result in chronic intestinal inflammation of the affected area of the gastrointestinal wall. Affected areas of the gastrointestinal wall, e.g. the large intestinal wall, of such chronic intestinal inflammation are the sites of inflammation. Particularly in the pathogenesis of UC, mucus layer impairment is considered an important factor. The term "mucus layer impairment" as used herein refers to the partial or complete loss of the mucus layer from the outermost epithelial layer of the mucosa.

Therefore, in one embodiment of the present invention, the topical treatment results in the increased uptake of the anti-TNFα antibody or functional fragment thereof into the large intestinal wall at sites of inflammation. In another embodiment of the present invention, the topical treatment results in the faster uptake of the anti-TNFα antibody or functional fragment thereof into the gastrointestinal wall at sites of inflammation. In yet another embodiment of the present invention, the topical treatment results in a faster penetration of the antibody specific to TNFα or functional fragment thereof into the deeper submucosal layer of the gastrointestinal wall at sites of inflammation. In a preferred embodiment it is the anti-TNFα antibody, for which the uptake is increased or faster, or for which the penetration is deeper at the site of inflammation.

The present inventors found that upon incubation of anti-TNFα antibodies or functional fragments thereof with the colonic tissue, although being taken up efficiently at the luminal side, no anti-TNFα antibodies or functional fragments thereof had left the large intestinal wall at the opposite side after 2 h incubation, indicating that the TNFα antibodies or functional fragments thereof are retained effectively in the colonic tissue. Therefore, in yet another embodiment of the present invention the topical treatment with the inventive composition results in a retention of the anti-TNFα antibody or functional fragment thereof in the gastrointestinal wall, with only minor systemic release into the rest of the body.

In one embodiment of the present invention, the composition for use in the topical treatment of the inflammatory bowel diseases provides a concentration of anti-TNFα antibody or functional fragment thereof in the large intestinal lumen of 0.02 mg/ml to 0.4 mg/ml. Further preferred concentrations in the large intestinal lumen in accordance with this embodiment are 0.05 mg/ml to 0.35 mg/ml, more preferably 0.1 mg/ml to 0.3 mg/ml, most preferably 0.15 mg/ml to 0.25 mg/ml, e.g. about 0.2 mg/ml. In another embodiment of the present invention, the composition for use in the topical treatment of the inflammatory bowel diseases provides a concentration of anti-TNFα antibody or the functional fragment thereof in the large intestinal lumen of 0.4 to 1 mg/ml. Further preferred concentrations in the large intestinal lumen in accordance with this embodiment are 0.5 mg/ml to 0.95 mg/ml, more preferably 0.6 mg/ml to 0.9 mg/ml, most preferably 0.75 mg/ml to 0.85 mg/ml, e.g. about 0.8 mg/ml.

In an alternative embodiment, the use of the inventive composition results in a decrease of a pH, in accordance with the pH values as defined in any one of the above embodiments, in the terminal ileum of the small intestine of a human patient. In another alternative embodiment, the use of the inventive composition provides a concentration of the anti-TNFα antibody or functional fragment thereof, in accordance with the concentrations as defined in any one of the above embodiments, in the terminal ileum of the small intestine of a human patient. Such a decrease in luminal pH and such concentrations in the terminal ileum are particularly beneficial for patients suffering from Crohn's disease. Thus, for these alternative embodiments the human patient is preferably a patient suffering from Crohn's disease.

According to the present invention a functional fragment of a TNFα-specific antibody can be used in the composition for use in the treatment of the inflammatory bowel diseases. As shown for the Fab fragment in example 6, the use of such a functional fragment allows the increased absorption into the large intestinal wall and can lead to the accumulation of the functional fragment in the mucosa and in the submucosa. Preferably, the functional fragment of the present invention is a Fab fragment, a F(ab')$_2$ fragment, a Fab' fragment, a scFv, a dsFv, a VHH, a diabody, a triabody, a tetrabody, a Fc fusion protein or a minibody.

In one embodiment of the present invention, the composition for use in the topical treatment of the inflammatory bowel diseases is administered orally. Oral administration in context of the present invention means the introduction of the composition into gastrointestinal tract via the mouth. In a preferred embodiment of the present invention the composition is a solid dosage form, preferably in the form of a pellet, granule, micro particle, nano particle, mini tablet, capsule or tablet coated with a coating material that prevents the release of the composition before the ileocolonic region of the intestine. The ileocolonic region is the region of the gastrointestinal tract where the small intestine merges with the large intestine, i.e. the terminal ileum.

Coating materials for the targeted release of a composition in the large intestinal lumen are known in the art. They can be subdivided into coating materials that disintegrate above a specific pH, coating materials that disintegrate after a specific residence time in the gastrointestinal tract and coating materials that disintegrate due enzymatic triggers specific to the microflora of the large intestine. Coating materials of these three different categories for targeting to the large intestine have been reviewed for example in Bansal et al. (Polim. Med. 2014, 44, 2, 109-118). These uses of such coating materials have also been described for example in WO2007/122374A2, WO0176562A1, WO03068196A1 and GB2367002A.

Preferred coating materials of the present invention are Poly vinyl acetate phthalate, Cellulose acetate trimellitate, Hydroxypropyl methylcellulose phthalate HP-50, Hydroxypropyl methylcellulose phthalate HP-55, Hydroxypropyl methylcellulose phthalate HP-55S, Hydroxypropyl methylcellulose acetate succinate, Cellulose acetate phthalate, Acrylic acid copolymer, Eudragit L100-55, Eudragit L30D-55, Eudragit L-100, Eudragit L12.5, Eudragit S-100, Eudragit S12,5, Eudragit FS30D, Hydroxyl propylethyl cellolose phthalate, PEG 6000, Ac-di-sol, Talc, Hydroxy propyl methyl cellulose acetate succinate (HPMCAS), Hydroxy ethyl cellulose, ethylcellulose, microcrystalline cellulose, Hydroxy propyl methyl cellulose, Chondroitin sulphate, Pectin, Guar gum, Chitosan, Lactose, Maltose, Cellobiose, Inulin, Cyclodextrin, Lactulose, Raffinose, Stachyose, Alginate, Dextran, Xantham gum, Guar gum, Starch, Tragacanth, Locust bean gum, Cellulose, Arabinogalactan, Amylose and combinations thereof.

In a different embodiment of the present invention, the composition for use in the topical treatment of the inflammatory bowel diseases is administered rectally. Rectal administration in context of the present invention means the introduction of the composition into gastrointestinal tract via the anus. In a preferred embodiment of the present invention the composition is used in the form of an enema, a gel, a foam or a suppository.

One unit dose of the composition may comprise an amount of active agent in the range of from about 0.1 mg to about 100 mg, or from about 1 mg to about 80 mg, or from about 10 mg to about 50 mg.

The composition of the present invention is preferably administered to the patient one to three times per day. In one embodiment, the composition is administered twice daily. In another embodiment, the composition is administered three times per day. Most preferably, the composition is administered once daily.

Another aspect of the present invention is the composition described herein for use in preventing an acute phase of the inflammatory bowel disease. In another aspect, the composition described herein is used for preventing flare-ups in a patient having inflammatory bowel disease in remission.

EXAMPLES

Materials and Methods Applied in the Examples
Human Colonic Model

A colonic model based on a mixed faecal inoculum was used to mimic the luminal environment of the human large intestine. The model was set up inside an anaerobic workstation (Electrotek 500TG workstation, Electrotek, West Yorkshire, UK) maintained at 37° C. and a relative air humidity of 70%. Three healthy human volunteers were given previously weighed plastic receptacles into which fecal samples were collected. The volunteers were on no medication and had not taken antibiotics for at least the previous six months. The fecal material was transferred in the anaerobic workstation and diluted with freshly prepared basal medium (as described in Hughes et al., 2008, FEMS Microbiol Ecol 64(3): 482-493) to obtain 15% w/w slurry by homogenization using an Ultra Turrax® (IKA T18 Basic) homogenizer at a speed of 18,000 rpm. The homogenized bacterial media was sieved through an open mesh fabric (SefarNitex®, pore size 350 μm) to remove any unhomogenised fibrous material. The pH and buffer capacity of the human fecal slurry was 6.8 and 28.3 mM/L/pH unit, respectively, which are in close agreement with human ascending colon values described in the prior art. The model has been widely used to evaluate the stability of small molecules and peptides in the colon. Moreover, the in-vivo relevance of this type of colonic model has been shown by Tannergren et al. (2008 Eur J Pharm Sci 57: 200-206) who achieved a good correlation between colonic drug degradation and fraction absorbed in the colon.

Size-Exclusion Chromatography (SEC)

Sample analysis was performed using a high performance liquid chromatography (HPLC) system (Agilent Technologies, 1260 Infinity) equipped with a pump (model G1311C), autosampler (model G1329B) and a diode-array UV detector (model G1314B). A 600×7.8-mm Biosep 5 μm SEC-s3000 400 A (Phenomenex, Torrance, Calif.) size exclusion (SE) chromatography column was used for sample separation using phosphate buffer saline (pH 7.3) prepared in sterile HPLC grade water as the mobile phase for elution, at a flow rate of 1 ml/min. The analysis was operated at room temperature and UV detection wavelength was set at 280 nm. Each sample was run for 40 minutes to allow complete elution of the sample proteins and reduce run-over. The retention time for IgG1 antibody, F(ab')2 and Fab/Fc fragments was 17, 18.2 and 20.3 minutes, respectively.

SDS-PAGE and Silver Staining

After separation on the SE-HPLC system, samples were withdrawn at their respective retention times and analysed for identification via molecular weight determination by SDS-PAGE using an XCell SureLock® Mini-Cell electrophoresis tank (ThermoFisher Scientific) and a Novex®Bis-Tris 4-12% precast gel (ThermoFisher Scientific). A 6 μl LDS sample buffer was added to 20 μl of sample solution and 20 μl of this mixture was added into the wells of the gel along with 3 μl of protein standard. A freshly prepared 10 times diluted running buffer solution was added and the gel was run at 200 V for 50 minutes. At the end of the run, the gel was carefully removed and added to 20 ml of coomassie blue stain for at least 1 hour with gentle shaking. Due to the low concentration of the intact antibody and the fragments formed, coomassie blue staining was not sufficient to clearly visualize the protein bands. Hence a silver staining was performed on the same gel after every analysis due to the high sensitivity of the method. The gel was washed twice with water for 5 minutes. The gel was fixed in 30% ethanol: 10% acetic acid: 60% water, twice for 15 minutes with gentle shaking. The gel was washed with 10% ethanol, twice for 5 minutes followed by water using the same cycle. After this, the gel was sensitized for 1 minute with sensitizer solution and then washed with water twice for 1 minute each. Staining of the gel was then performed for 30 minutes in the staining solution followed by washing twice for 20 seconds each with water. The gel was then incubated in a developer solution (25 ml/gel) for 2-3 minutes till the bands start to appear clearly. The action was stopped by addition of 5% acetic acid solution for 10 minutes.

Tissue Samples

All experiments using rat tissue samples were approved by the University College London (UCL) School of Pharmacy's ethical review committee and were conducted in accordance with the UK home office standards under the Animals (Scientific Procedures) Act, 1986. Male 6-8 wk-old Wistar rats (Harlan UK Ltd, Oxfordshire, UK) weighing 200 to 250 g were used. The animals were housed at controlled temperatures with light-dark cycles, fed standard mice chow pellets, had access to tap water from bottles, and were acclimatized before being studied. The rats were sacrificed by placing the animal in a CO2 chamber for 5 minutes.

Ussing Chamber Studies

The tissue segment was collected from the ascending colon of a male wistar rat and transferred to an ice cold solution of Krebs-Bicarbonate Ringer solution (KBr) of pH 7.4. The tissue was cut open transversally and was washed with KBr solution to remove the luminal content and was mounted on the Ussing chambers (Harvard Apparatus, Cambridge, UK). The system consists of an apical chamber representing the luminal side (mucosal) of the tissue, and a basolateral chamber representing the blood side (serosal). The exposed tissue area on each side of the chamber was 0.29 cm$^2$ and the tissue mounting region was 4×8 mm. The volume of KBr in each chamber was 3 ml and the pH was maintained at 7.4. The working system consists of a unit to fit a maximum of six vertical chambers, a gas manifold for carbogen purging (95% O2, 5% CO2) and a heater block to maintain the temperature of the chambers at 37° C. during the experiments with the use of a circulating water bath.

The tissue was incubated with KBr for 20 minutes before addition of the drug. Infliximab (commercially available mouse-human IgG1:K-chimeric anti-TNFα monoclonal antibody [mAb]) and adalimumab (commercially available human IgG1 anti-TNFα monoclonal antibody) concentrations tested during the permeation experiments was 2 mg/ml, 0.8 mg/ml and 0.2 mg/ml. Concentrations of infliximab and adalimumab Fab fragments tested during of permeation experiments was 0.2 mg/ml and 0.8 mg/ml. The antibodies and Fab fragments were added in the apical chamber of the Ussing chamber system facing the luminal (mucosal) side of the tissue and were incubated for 2 hours, unless specified otherwise for different time point studies. The tissue without drug was incubated in parallel for the same time which acted as the control. The chambers were purged with 95% O$_2$, 5% CO$_2$ and kept at 37° C. by water jackets during incubation. Samples (150 µl) were withdrawn from both compartments at hourly time points and were added to a protease inhibitor cocktail (450 µl) to quantify the amount of IgG or Fab fragment that had penetrated into the tissue from the apical chamber. The transepithelial electrical resistance (TEER) was continuously monitored during the experiment to confirm the viability and integrity of the tissue. Tissues with TEER value below 200 were not used for the permeation experiments.

Cryosectioning, Secondary Antibody Staining and Confocal Laser Scanning Microscopy (CLSM)

The tissue section exposed to the antibodies or Fab fragments was gently cut at the end of the experiment and immediately transferred to a cryostat (Leica CM3050, Leica Microsystems, Milton Keynes, UK) at −20° C. The tissue was allowed to freeze for 15-20 minutes. After the tissue was frozen, thin sections of tissue (10 µm) were sliced and mounted on adherent microscope slides (SuperFrost® Plus, VWR International, Leuven, Belgium). Up to 6 sections from the tissue exposed to the drug and 2 sections from the control tissue without drug were sliced. The slides were kept at room temperature for 15 minutes before starting the staining procedure. The tissue sections were fixed in 4% paraformaldehyde (Sigma-Aldrich, UK) for 10 minutes followed by incubation with 0.1% Triton X-100 (Sigma-Aldrich, UK) surfactant for 5 minutes to open up the tight junctions. The sections were then incubated with 1% bovine serum albumin (BSA) (Sigma-Aldrich, UK) for 30 minutes to avoid non-specific binding. Washing steps were included at every stage using Phosphate-buffered saline (PBS). The sections were then stained with secondary antibody, 10 µg/ml, (Red) (anti-human IgG from goat, Alexa Flour® 633, Molecular Probes, UK) for 1 hour. This was followed by staining with CellMask green plasma membrane stain (Green) (Molecular Probes, UK) (0.5× solution in PBS) at 37° C. for 1 minute to stain the cell components including cell membrane and the cytoplasm. The sections were then stained with Vectashield® Hard Set mounting medium with DAPI (Blue) (Vector Laboratories, Inc., Burlingame, Calif., USA) to stain the cell nuclei. The slides were stored at 2-8° C. in the dark until analysis by CLSM (LSM 710, Zeiss, Cambridge, UK). The images were processed and analysed by Zen 2012 imaging software (Carl Zeiss Ltd., Cambridge, United Kingdom).

Colonic Mucus Layer Impairment

Freshly excised male Wistar rat tissue samples from ascending and descending colon were exposed to a 10% w/v solution of mucolytic N-Acetyl-L-cysteine (NAC) (Sigma-Aldrich, UK) for 10 mins at room temperature in a petri dish. The NAC solution was prepared in PBS and dissolved by heating to 40° C. After exposure to NAC, the colon tissue mimics an injured/compromised mucus barrier state and acts as a local model of mucus barrier dysfunction. The concentration of NAC used and the time of incubation with the tissue samples were based on earlier studies by Qin and colleagues that showed 10% concentration and 10 minutes of exposure time to be sufficient to injure the mucus layer and reduce the mucosal hydrophobicity (Qin et al., 2008, Shock 29(3): 372-376). The current model is non-invasive and prevents any potential morphological damage to the epithelium that can be caused by physical scrapping or suction method to remove mucus layer, allowing the investigation of mucus layer as barrier.

Antibody Digestion

Figure 9:
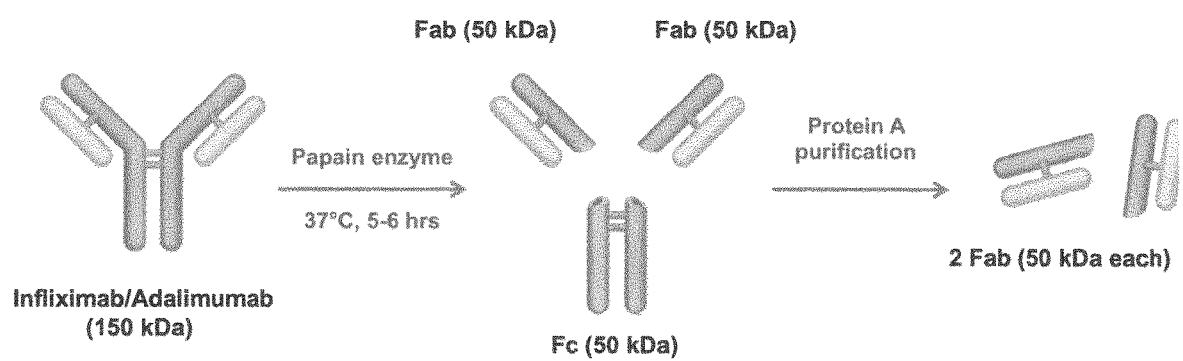
FIG. 9: Schematic representation of the digestion process of infliximab and adalimumab.

Infliximab or adalimumab was proteolytically digested using Immobilised papain (Thermo Fisher Scientific, cat no. 20341). A schematic representation of the digestion process is shown in FIG. 9. The digestion buffer consisted of Sodium Phosphate Monobasic (Sigma Aldrich, cat no. S8282-500G), Ethylenediaminetetraacetic acid, dihydrate (EDTA, Fisher Scientific, cat no. BP120-500) and L-Cysteine Hydrochloride Monohydrate (Fluka, cat no. 30129). The pH of the buffer was adjusted using Sodium Hydroxide solution (1.0 M, Merck, cat no. HC267016) or Hydrochloric acid (1.0 M, Fisher Scientific, cat no. J/4320/15). Purification of the digested antibodies was performed using NAb™ Protein A spin column (Pierce, cat no. 81956). Fab and Fc fragments of antibodies were eluted using Protein A. IgG binding buffer (1.0 M Tris buffer with EDTA, pH 8.0; Thermo Scientific, cat no. 21007) and IgG elution buffer (1.0 M Tris buffer, pH 8.5; Thermo Scientific, cat no. 21004). Neutralizing buffer (1.0 M Tris buffer, pH 8.5, Thermo Scientific).

Human Tissue Collection

Biopsy sample was collected from a colon cancer patient undergoing surgical resection. The subject had signed a written consent form to allow the use of the tissue sample for research purpose. The biopsy was collected from the region around the tumor in the ascending colon segment that was non-pathological and considered as histologically normal intestinal mucosa sample. The surgery was carried out at The Royal London Hospital, Queen Mary University of London, and the tissue sample was immediately used for Ussing chamber incubation study carried out at the Wingate Institute of Neurogastroenterology.

Results

Example 1

Infliximab and adalimumab (mAbs) were tested in the presence of human colonic bacteria mimicking the human large intestine. The stability of infliximab and adalimumab in human colonic conditions is shown in FIG. 1. After 1 hour, 75% of the dose of infliximab was detected. After 2 hours, almost 40% of the dose of infliximab was intact (t1/2=96.08±7.60 min). In the case of adalimumab, 50% of the dose was fragmented after 1 hour while 20% of the dose remained unchanged after 2 hours (t1/2=54.35±0.18 min). A proportion of both mAbs had fragmented into F(ab')2, Fab and Fc fragments. This results shows that in the human colonic model infliximab and adalimumab can be expected to have high stability in the human colon, where the degradation of the intact structure is mainly accounted for by formation of F(ab')2 and Fab fragments and only to a lower extent by degradation into therapeutically inactive smaller peptides.

Example 2

Figure 2:
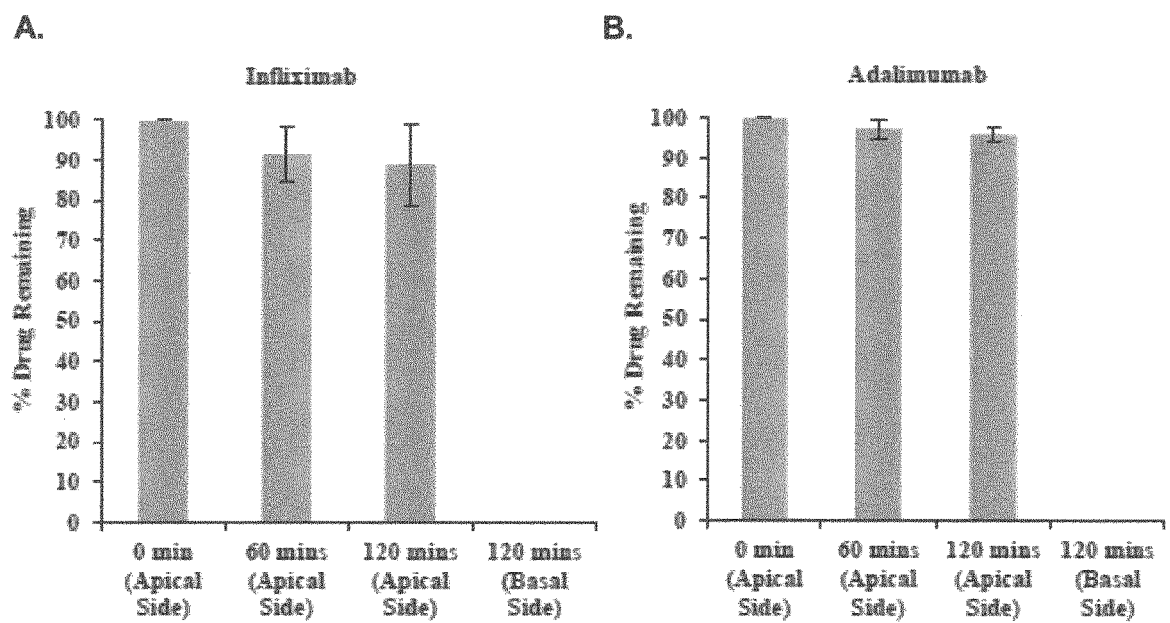
FIG. 2: SE-HPLC data of infliximab and adalimumab in the apical and basolateral compartment of the Ussing chamber at different time points, respectively. A) Percentage antibody, remaining on the apical side of a rat ascending colon tissue segment fixed in an Ussing chamber system, applied at a concentration of 2 mg/ml and quantified at different time points, using A) infliximab or B) adalimumab. The quantification of antibodies remaining on the apical and basolateral side was performed by size exclusion high performance liquid chromatography (SE-HPLC). Each value represents mean±standard deviation (S.D.) (n=3).

Penetration of infliximab and adalimumab in rat ascending colon tissue at 2 mg/ml The ability of chimeric IgG1 infliximab and human IgG1 adalimumab to penetrate the colonic tissue at an incubation concentration of 2 mg/ml was investigated using a rat ascending colon tissue segment fixed in an Ussing chamber system. Following incubation, cryosectioning and staining with the secondary antibody, the tissue sections were analysed by confocal microscopy. The concentration of 2 mg/ml was selected to study the effect of high concentration of mAb on the ability to penetrate into the colon tissue. Using SE-HPLC the amount of infliximab and adalimumab dose penetrating into tissue was quantitatively estimated by measuring the amount of mAb that have left the apical side of the Ussing chamber system, penetrating into the tissue, at different time points during incubation (FIG. 2).

Figure 3:
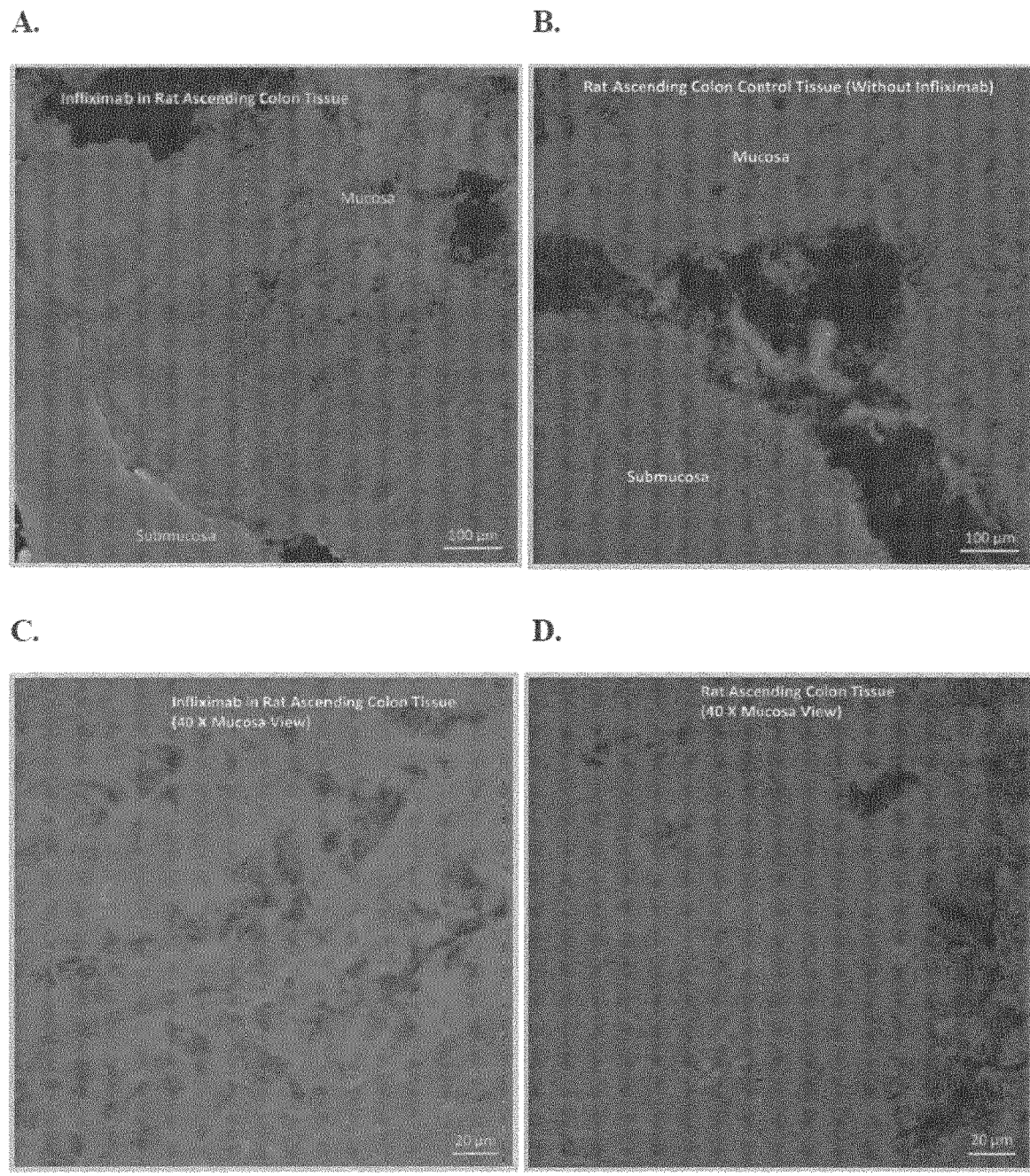
FIG. 3: Confocal laser scanning microscopy (CLSM) of the penetration of infliximab in ascending colon tissue at apical concentration of 2 mg/ml (n=3). Infliximab was stained red with goat anti-human IgG secondary antibody, cell components were stained green and nuclei were stained blue with DAPI. A) Infliximab penetration in the colon tissue (10× resolution). B) Colon tissue without exposure to infliximab as negative control (10× resolution). C) Infliximab penetration in the mucosa region at 40× resolution. D) Mucosa region of colon tissue without infliximab exposure (40× resolution).
Figure 4:
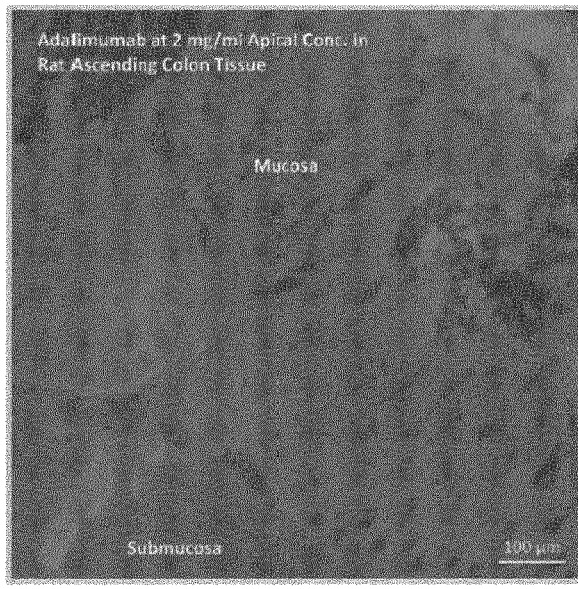
FIG. 4: CLSM of the penetration of adalimumab in ascending colon tissue at apical concentration of 2 mg/ml (n=3). Adalimumab was stained red with anti-human IgG secondary antibody, cell components were stained green and nuclei were stained blue with DAPI. A) Adalimumab in the colon tissue (10× resolution). B) Colon tissue without exposure to Adalimumab as negative control (10× resolution). C) Adalimumab penetration in the mucosa region at 40× resolution. D) Mucosa region of colon tissue without adalimumab exposure (40× resolution).
Figure 4:
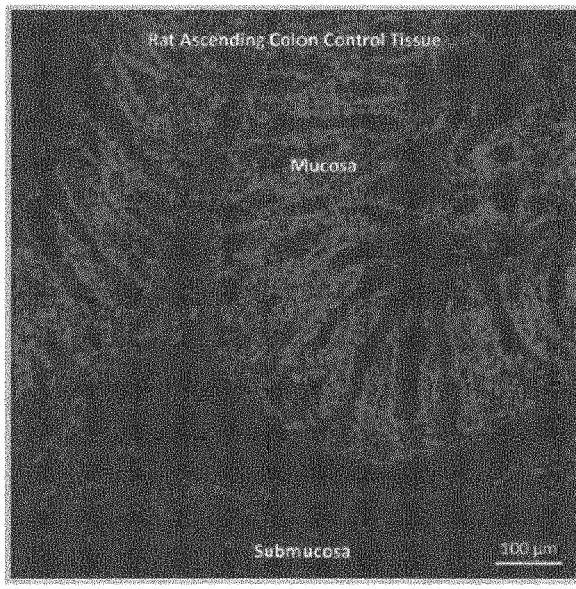
Figure 4:
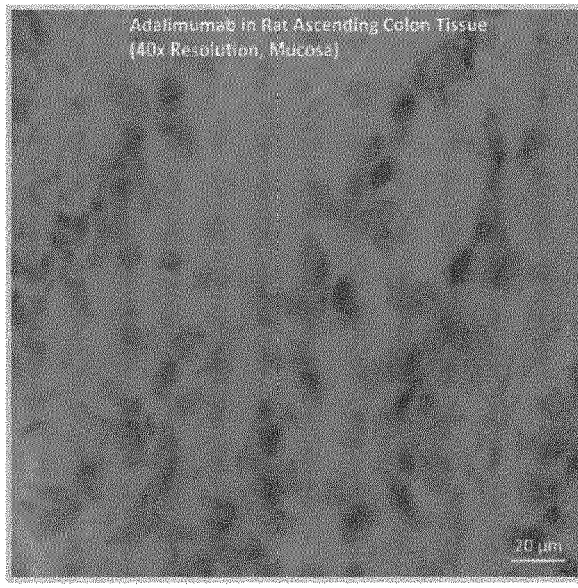
Figure 4:
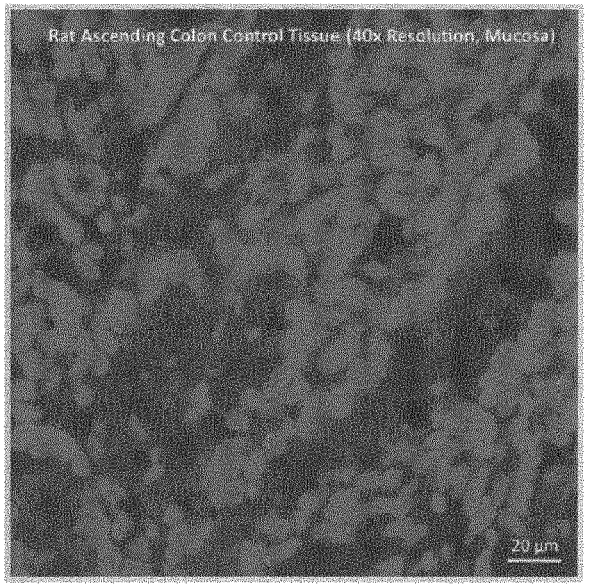

Approximately 10% (0.2 mg/ml) and 6% (0.12 mg/ml) of the incubation concentration of infliximab and adalimumab respectively was reduced at the apical compartment at the end of 2 h incubation. No drug was detected on the basolateral side at the end of 2 h incubation. This shows that the antibodies were potentially retained in the colon tissue for at least 2 h with no permeation across to the basolateral side. Analysis of the CLSM images of the tissue sections at the end of the Ussing chamber incubation experiment revealed localisation of the mAbs in the ascending colon tissue (FIG. 3A, C). A significant proportion of the infliximab dose was shown to be trapped in the mucus layer overlying the epithelial cells. However, the confocal images also showed that a proportion of the dose was able to penetrate through the mucus layer deeper into the epithelial cells of the mucosa and a proportion of the dose was also able to reach the submucosal region of the colonic tissue. The control tissue that was fixed in the Ussing chamber system without exposure to mAbs was stained with the same procedure as the tissue exposed to the drug and showed some but very little background signal due to non-specific binding of the secondary antibody with the tissue components (FIG. 3B, D). A similar trend was observed with adalimumab with high signal observed in the mucosal and submucosal regions (FIG. 4A, C) compared to control (FIG. 4B, D).

Example 3

Figure 5:
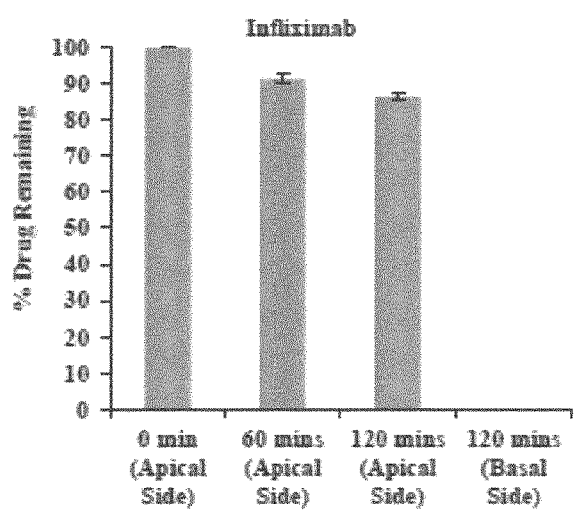
FIG. 5: A) SE-HPLC data of infliximab and adalimumab in the apical and basolateral compartment at different time points, respectively. Percentage antibody, remaining on the apical side of a rat ascending colon tissue segment fixed in an Ussing chamber system, applied at a concentration of 0.8 mg/ml and quantified at different time points, using A) infliximab or B) adalimumab. Each value represents mean±S.D. (n=3).
Figure 5:
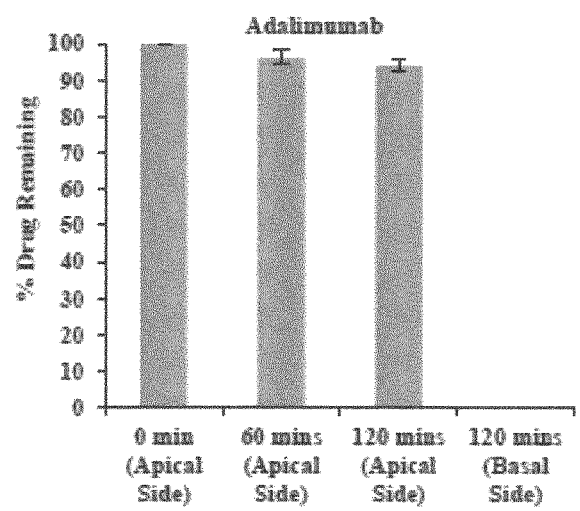
Figure 6:
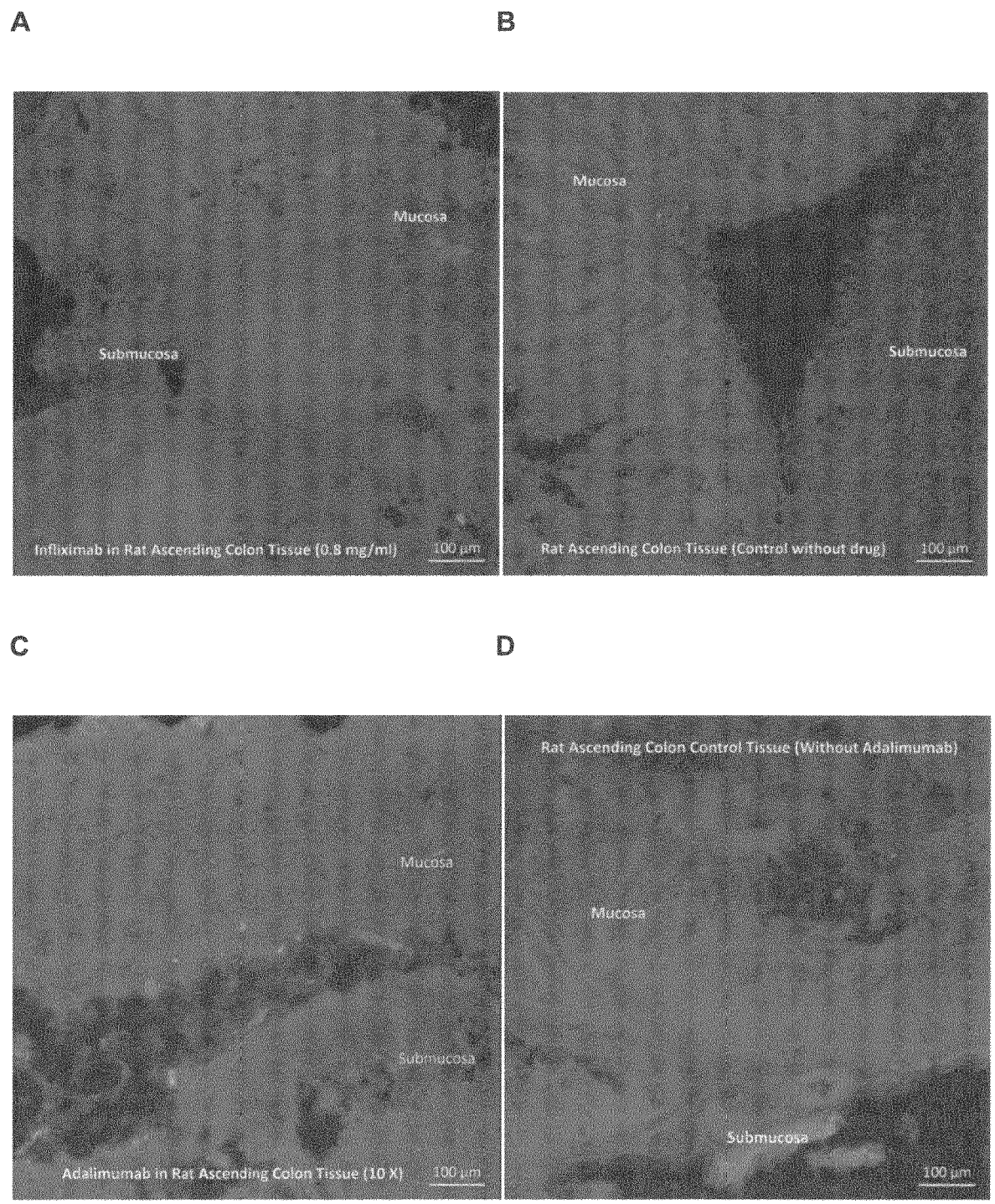
FIG. 6: CLSM of ascending rat colon tissue sections, at the end of the Ussing chamber incubation experiment with 0.8 mg/ml antibodies, following cryosectioning and staining. Infliximab and adalimumab were stained red with anti-human IgG secondary antibody, cellular components were stained green and nuclei were stained blue with DAPI. A) Infliximab penetration into colon tissue. B) Colon tissue without infliximab incubation. C) Adalimumab penetration in the colon tissue. D) Colon tissue without adalimumab incubation.

Penetration of infliximab and adalimumab in rat ascending colon tissue at 0.8 mg/ml The ability of mAbs infliximab and adalimumab to penetrate the colonic tissue at a concentration of 0.8 mg/ml was investigated using the same experimental setup as in example 2. Approximately 14% (0.11 mg/ml) and 5% (0.04 mg/ml) of the incubation concentration of infliximab and adalimumab was reduced in the apical compartment, respectively, at the end of 2 hours (FIG. 5). To correlate the SE-HPLC data with qualitative tissue levels of infliximab and adalimumab, the tissue sections were analysed by CLSM of the tissue sections (FIG. 6). Infliximab was able to penetrate into the mucosa, and a fraction of the dose was also detected in the submucosal region of the colon tissue. Adalimumab signal was also detected in the mucosal layer, indicating drug penetration into the colon tissue. However, compared to the higher apical concentration (2 mg/ml), the current concentration showed lower drug signal in the colon tissue segments. Despite higher infliximab dose reduction in the apical compartment compared to adalimumab, no difference in the qualitative drug levels and localization was observed by confocal laser scanning microscopy. Minimal background signal was observed with the negative control tissue samples when stained with the secondary antibody (FIGS. 6B & D).

Example 4

Figure 7:
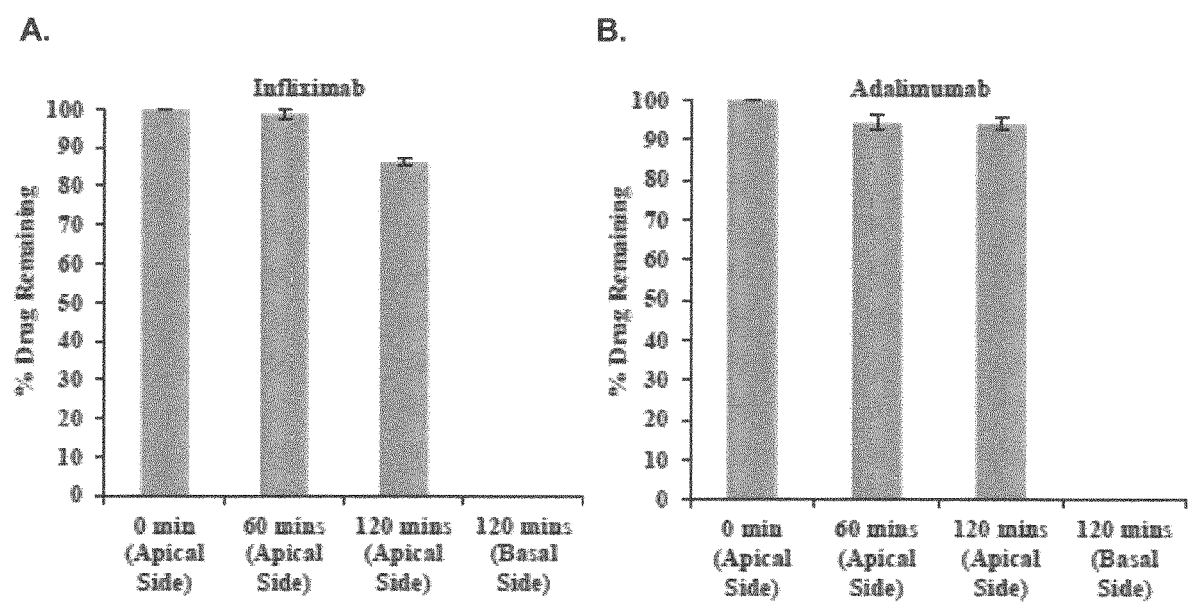
FIG. 7: A) SE-HPLC data of infliximab and adalimumab in the apical and basolateral compartment at different time points, respectively. Percentage antibody remaining on the apical side of a rat ascending colon tissue segment fixed in an Ussing chamber system, applied at a concentration of 0.2 mg/ml and quantified at different time points, using A) infliximab or B) adalimumab.
Figure 8:
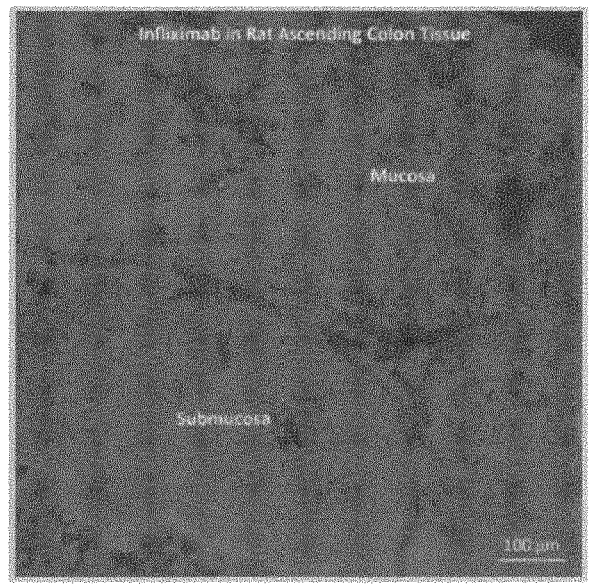
FIG. 8: CLSM of ascending rat colon tissue sections, at the end of the Ussing chamber incubation experiment with 0.2 mg/ml antibodies, following cryosectioning and staining. Infliximab and adalimumab were stained red with anti-human IgG secondary antibody, cellular components were stained green and nuclei were stained blue with DAPI. A) & B) Infliximab penetration into colon tissue. C) & D) Adalimumab penetration in the colon tissue. Both incubation studies were done in triplicates.
Figure 8:
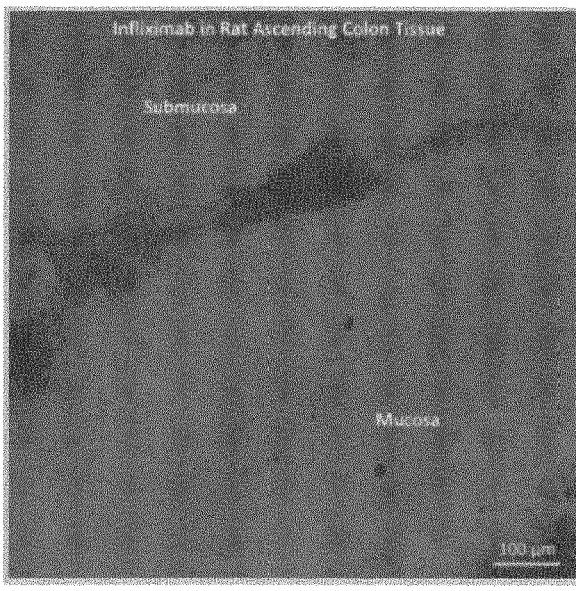
Figure 8:
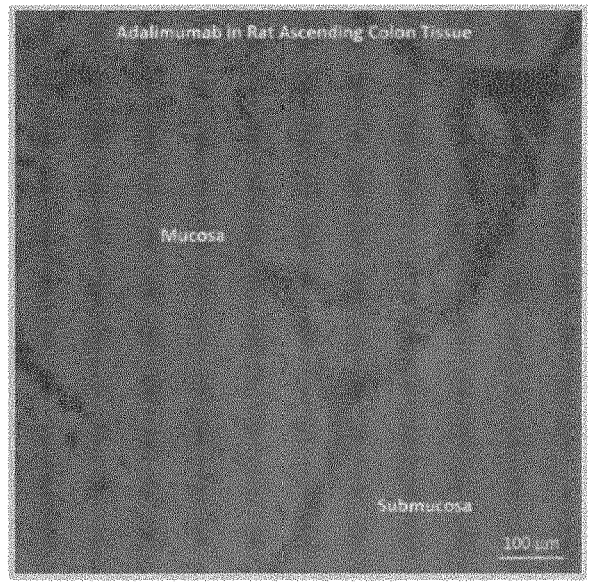
Figure 8:
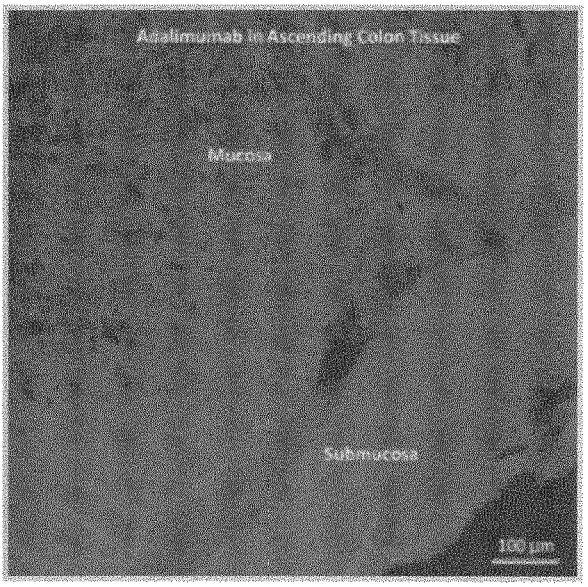

Penetration of infliximab and adalimumab in rat ascending colon tissue at 0.2 mg/ml The ability of infliximab and adalimumab to penetrate into colonic tissue at an incubation concentration of 0.2 mg/ml was investigated using rat ascending colon tissue segment fixed in the Ussing chamber system using the same experimental setup as examples 2 and 3. Approximately 14% (0.03 mg/ml) and 6% (0.01 mg/ml) dose of infliximab and adalimumab was reduced at the apical compartment, respectively, at the end of 2 h (FIG. 7). To determine the correlation of the reduction in apical concentration with qualitative drug signal in the tissue, confocal laser scanning microscopy analysis was performed. The CSLM images of the tissue sections are shown in FIG. 8. Interestingly, both infliximab and adalimumab were detected in the mucosal and submucosal regions of the colon tissue with no difference in drug signal or regional localisation between the two antibodies. The control tissue without exposure to drug showed minimal background signal with the secondary antibody (data not shown). The current data showed that despite mAbs being highly hydrophilic in nature, they are able to permeate across the hydrophobic outer and the inner mucus layers to penetrate deeper in the mucosal and submucosal regions of the colon tissue at all three concentrations tested.

Example 5

Penetration of infliximab and adalimumab in rat ascending colon tissue at 0.02 mg/ml The lowest concentration of mAbs evaluated in the current set of apical concentration studies was 0.02 mg/ml. However, at this concentration SE-HPLC was found not to be an accurate method of indirectly predicting antibody penetration into the tissue by measuring reduction of antibody concentration in the apical compartment. CLSM images of the penetration of infliximab and adalimumab in the colon tissue showed for both mAbs a significantly lower signal in the penetration studies at the lowest concentration compared to the higher apical concentrations (data not shown). Infliximab was shown to penetrate at low levels into the mucosa and submucosa regions of the colon tissue. However, adalimumab showed little or no detectable signal in both regions of the colon tissue. The control tissue without exposure to the mAbs showed no signal.

Example 6

Tissue Penetration of Infliximab Fab Fragment

Figure 10:
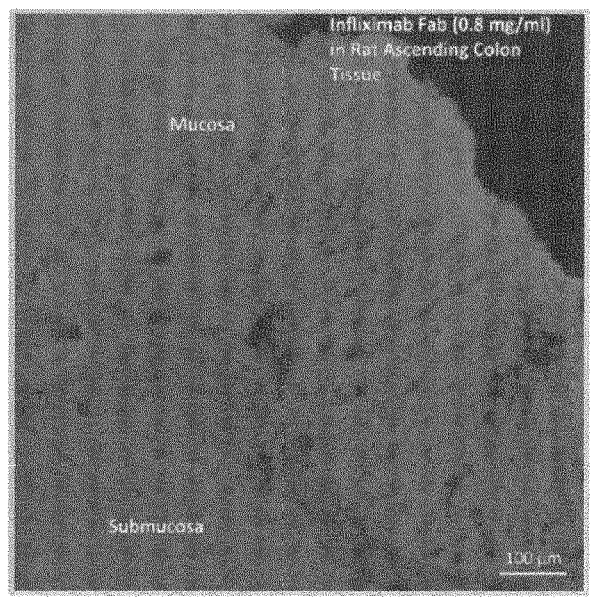
FIG. 10: A)-C) Penetration of infliximab Fab fragment in the rat ascending colon tissue segment at apical concentration of 0.8 mg/ml. D) Control tissue without exposure to infliximab Fab fragment but stained with secondary antibody showing no background signal. The study was done in triplicates.
Figure 10:
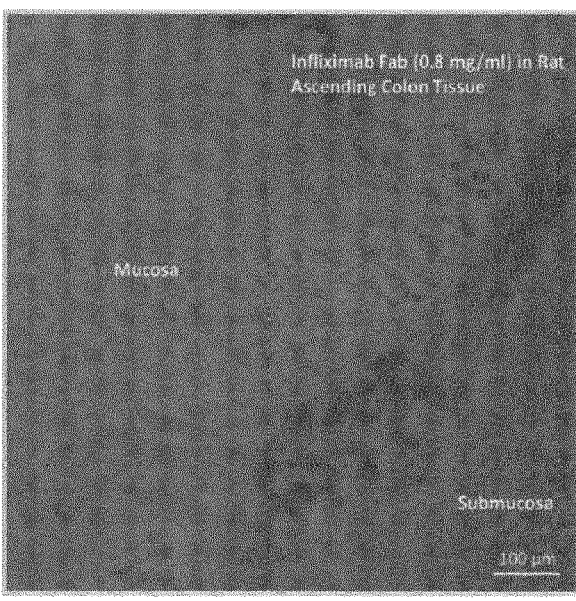
Figure 10:
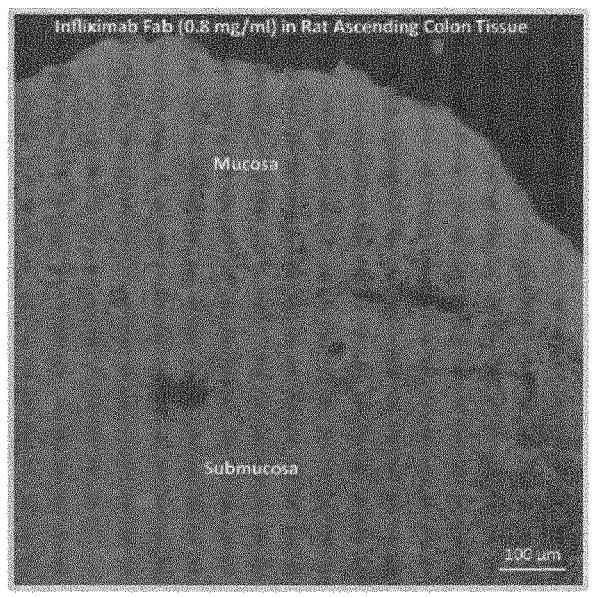
Figure 10:
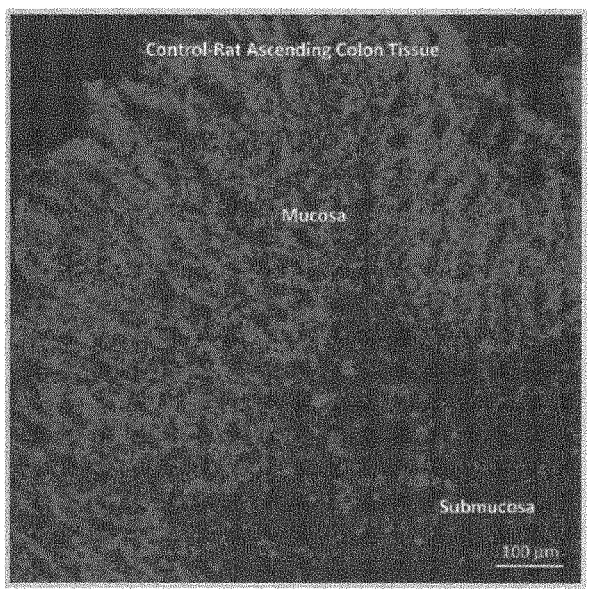
Figure 11:
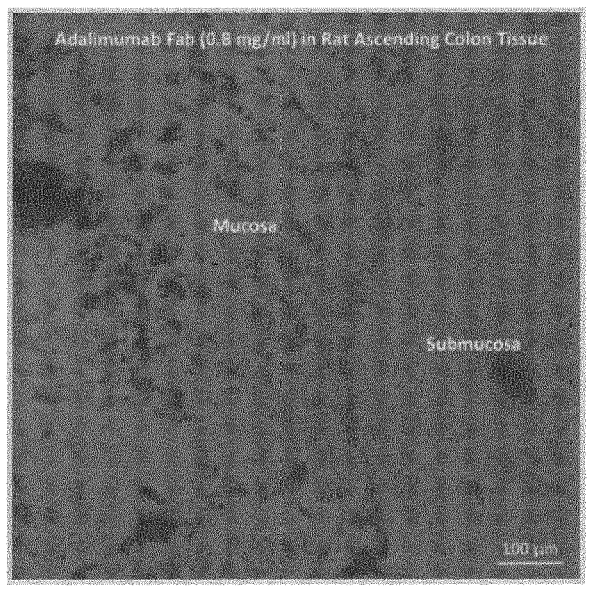
FIG. 11: A)-C) Penetration of adalimumab Fab fragment in the rat ascending colon tissue segment at apical concentration of at 0.8 mg/ml apical concentration into rat ascending colon tissue segments fixed in an Ussing chamber system. D) Control tissue without exposure to adalimumab Fab fragment but stained with secondary antibody showing no background signal. The study was done in triplicates.
Figure 11:
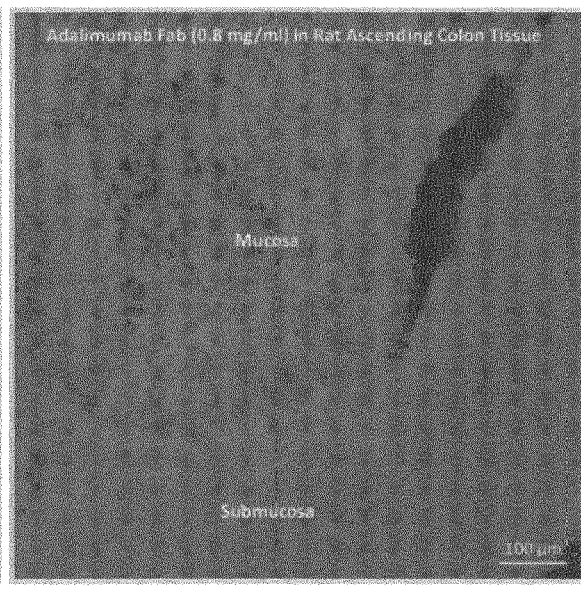
Figure 11:
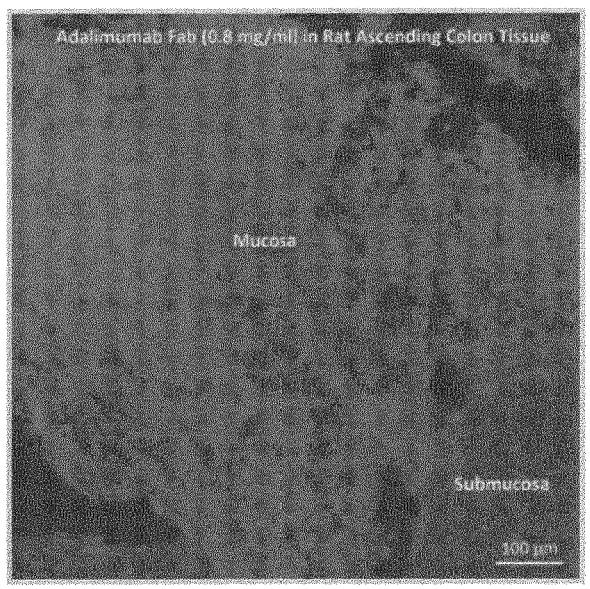
Figure 11:
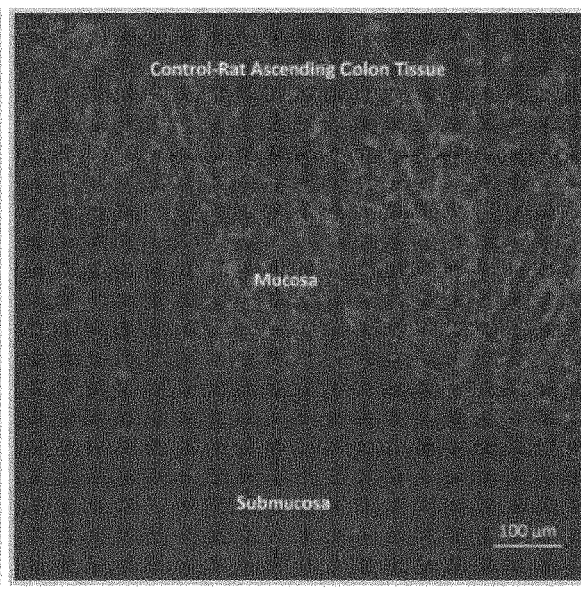
Figure 12:
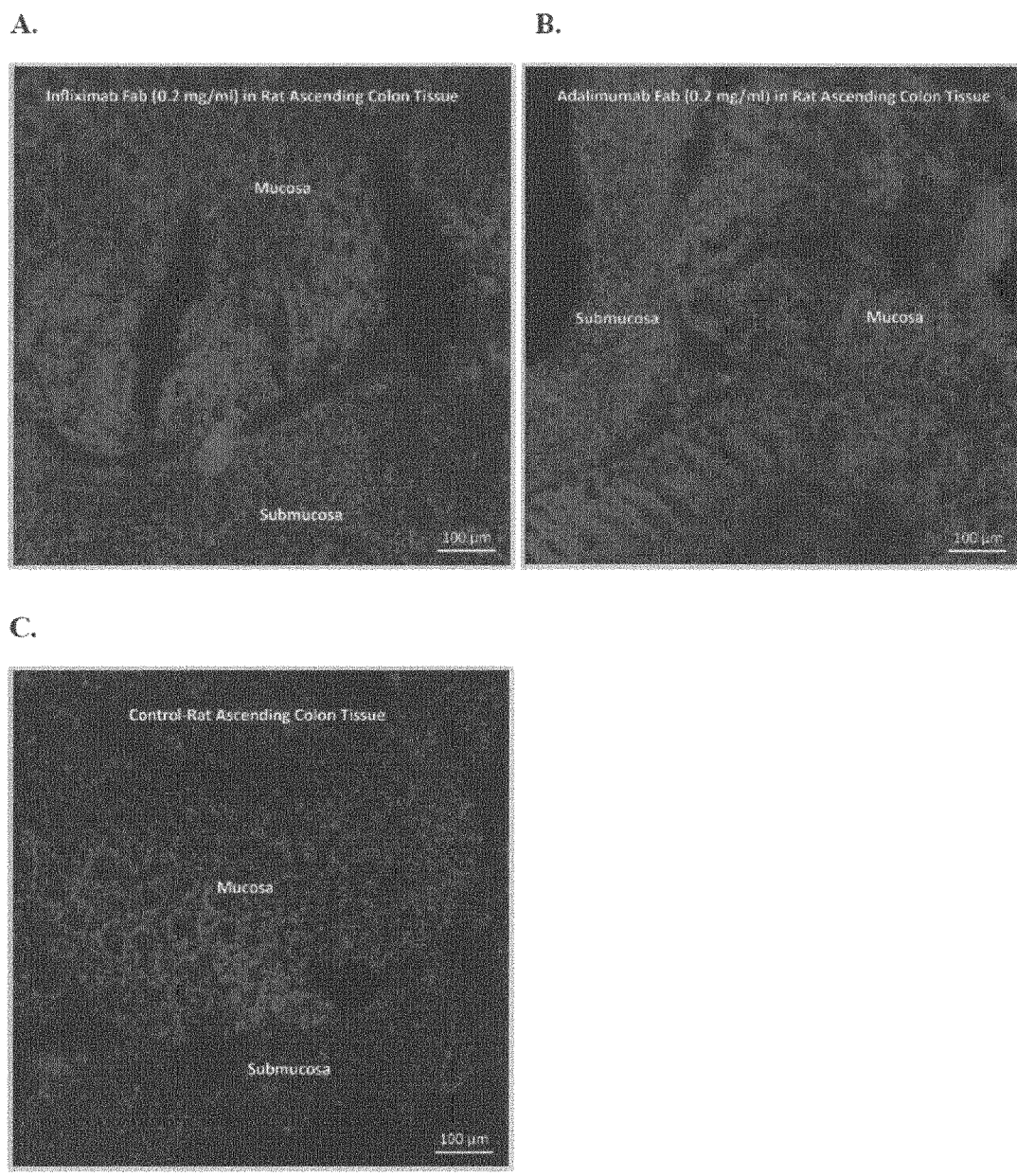
FIG. 12: A) & B) Penetration of infliximab and adalimumab Fab fragments at 0.2 mg/ml apical concentration into rat ascending colon tissue segments fixed in an Ussing chamber system. C) Control tissue without exposure to infliximab/adalimumab Fab fragment but stained with secondary antibody showing no background signal. The study was done in triplicates.

Infliximab was digested by papain mediated digestion to obtain purified Fab fragments of the mAb (FIG. 9). The Fab fragments were tested for purity by SDS-PAGE and SE-HPLC and for binding affinity to the secondary antibody by dot-blot for localisation in the tissue by confocal microscopy. The Fab fragments of infliximab and adalimumab were tested for penetration into the rat ascending colon tissue segment at apical concentrations of 0.8 mg/ml and 0.2 mg/ml, respectively. The colon tissues retained their tight junction integrity during the incubation with infliximab and adalimumab Fab fragments at both apical concentrations. At 0.8 mg/ml apical concentration, both antibody Fabs showed the ability to penetrate across the mucus layer in the colon tissue with high signal observed in both the mucosal and submucosal regions (FIGS. 10 & 11). Minimal background signal was observed in the control tissue samples without exposure to the Fabs. At apical concentration of 0.2 mg/ml, a lower signal was detected for both infliximab and adalimumab Fab fragments in the colon tissue, although also at this concentration both antibodies penetrated to both the mucosal and submucosal regions (FIG. 12). The high tissue penetration of Fab fragments has potential therapeutic relevance since Fab is the antigen binding region that can bind to the epitope on TNFα, preventing the interaction of TNFα with its receptor, which could bring about an anti-inflammatory response. At both apical concentrations, no permeation of Fab fragments was observed across the tissue in to the basolateral compartment that was confirmed by SEC (data not shown).

Example 7

Figure 13:
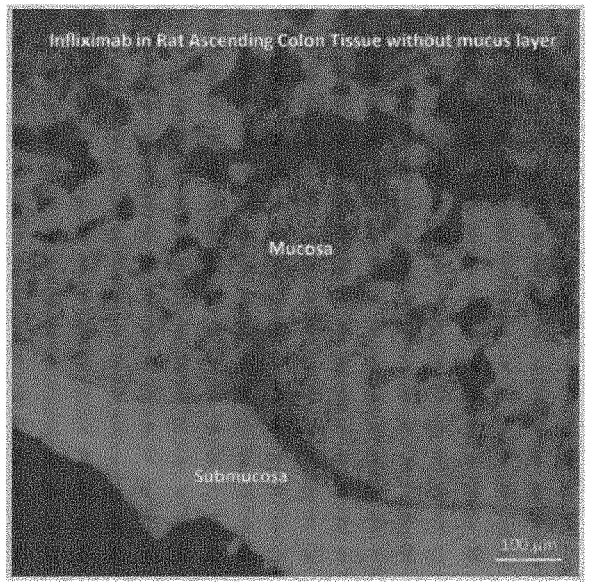
FIG. 13: A) & B) Penetration of infliximab in rat ascending and descending colon tissue respectively with impaired mucus layer in an Ussing chamber system. C) & D) Adalimumab penetration in ascending and descending colon tissue respectively with impaired mucus layer.
Figure 13:
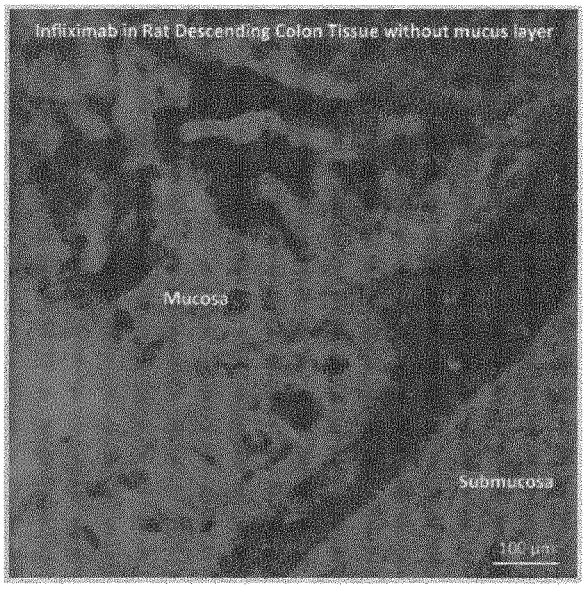
Figure 13:
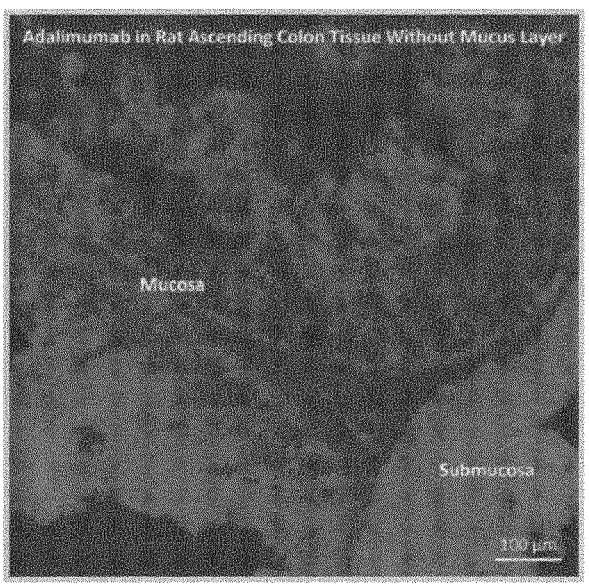
Figure 13:
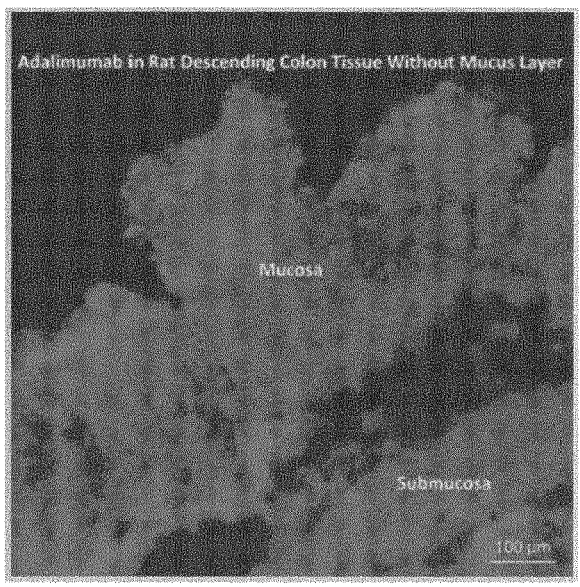

Impaired Mucus Barrier Compared to Intact Mucus Barrier in Ascending Vs Descending Colon FIG. 13 shows the penetration of infliximab and adalimumab mAbs in ascending and descending colon tissue samples with an impaired mucus layer post treatment with NAC solution. Both mAbs were tested in ascending and descending colon regions of the same animal for direct comparison of the regional differences (n=3). The apical concentration of mAbs was selected to be 0.2 mg/ml since at this concentration. Interestingly, the drug signal was significantly higher in both ascending and descending colon regions with impaired mucus layer compared to colon tissue with intact mucus layer. This trend was similar in all three rats with impaired mucus layer compared to the three rats with intact mucus layer, confirming that mAbs are able to penetrate both proximal and distal regions of the large intestine, and that in both regions impaired mucus layer results in an increased uptake of the mAbs. Similar results were observed when both antibodies were tested on colon tissue from the same rat. Moreover, no permeation of mAbs was observed across the colon tissue onto the basolateral compartment by performing SEC, showing drug retention in the tissue with impaired mucus layer. The experiment was repeated with Fab fragments of infliximab and adalimumab. For that ascending colon tissue at an apical concentration of the Fabs of 0.2 mg/ml was incubated in the presence and absence of intact mucus layer. Also here a similar trend was observed, with higher uptake into the colon tissue with impaired mucus layer compared to intact mucus layer, although the effect was less pronounced (data not shown).

Example 8

Time Taken for the Penetration of mAbs in the Colon Tissue

In previous examples the penetration of infliximab and adalimumab mAbs in the colon tissue was evaluated at the end of 2 h incubation in the Ussing chamber system. In the present example the level of penetration in the ascending colon tissue after 30 mins, 1 h and 2 h incubation time at an apical concentration of mAbs of 0.2 mg/ml. In order to take samples for confocal microscopy analysis, three Ussing chamber incubations were performed in parallel that were stopped at 30 mins, 1 h and 2 h respectively. Colon tissue sample for all three incubations was taken from the same animal to directly compare the penetration of antibody after the 3 different time points. The study was conducted in a total of 3 rats. Infliximab was shown to consistently penetrate into the mucosal region of the colon tissue within 30 mins of incubation in all the studies. In 1 h incubation studies, infliximab showed deeper penetration into the colon tissue with drug signal detected in the mucosa and submucosa. This penetration enhanced as the incubation time increased to 2 h. No permeation of infliximab to the basolateral compartment was observed, as measured by SEC. The same study design was used to investigate the time taken for the antibody to penetrate the ascending colon tissue with an impaired mucus barrier following treatment with NAC. A high drug signal was observed in the ascending colon tissue already after 30 mins of incubation throughout the mucosal and submucosal region (data not shown). This was significantly higher than the penetration of infliximab observed in the colon tissue with intact mucus layer after the same time point.

Example 9

Figure 14:
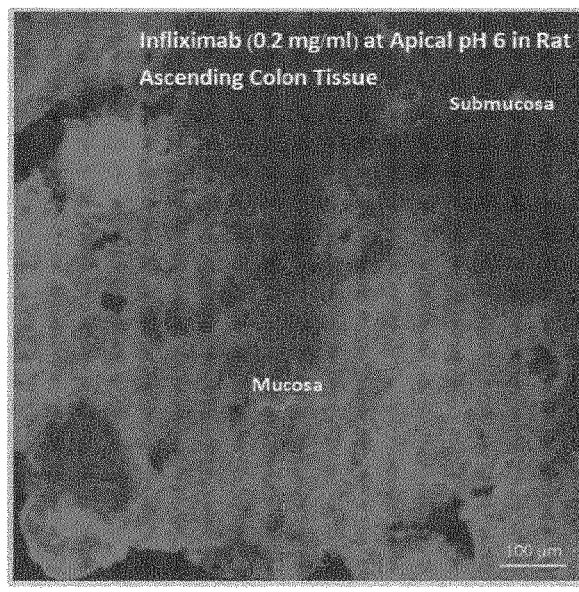
FIG. 14: CLSM of ascending rat colon tissue sections incubated with 0.2 mg/ml infliximab antibodies at pH 6 or 7.4. Only antibody signal is shown. A) & B) Penetration of infliximab in rat ascending colon tissue at apical pH 6. C) & D) Penetration of infliximab in rat ascending colon tissue at apical pH 7.4 (n=3).
Figure 14:
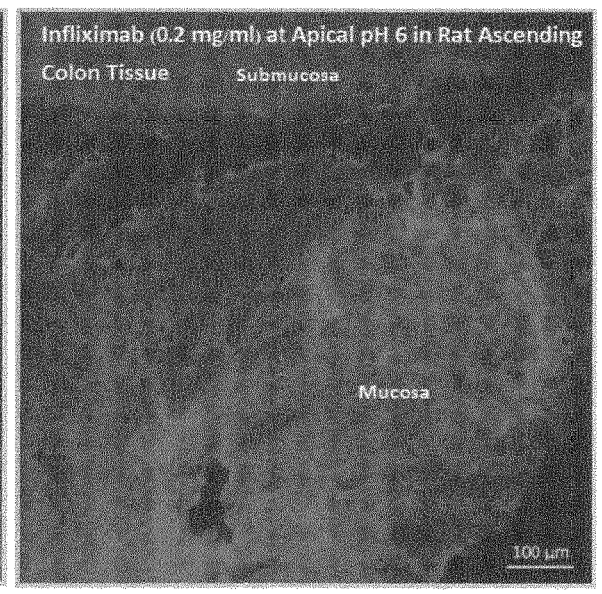
Figure 14:
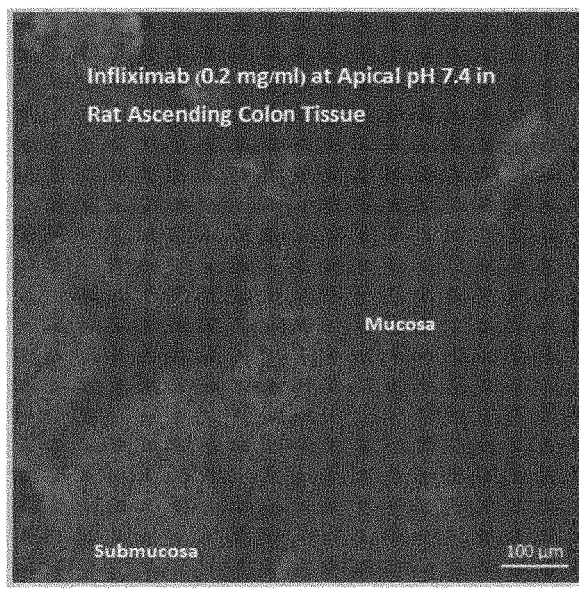
Figure 14:
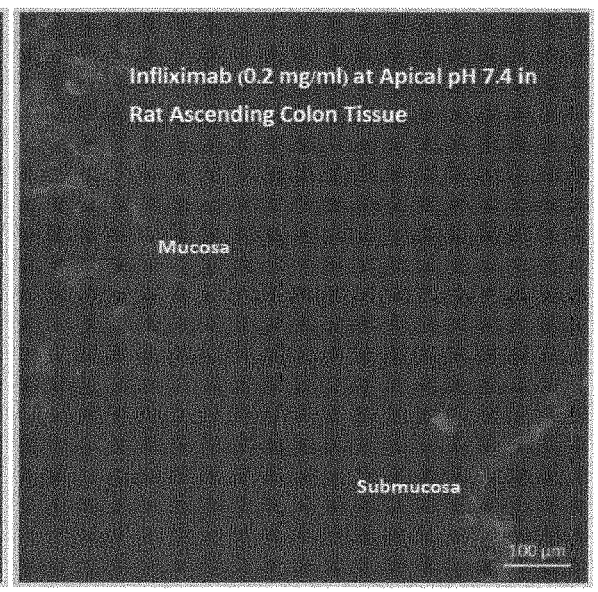
Figure 15:
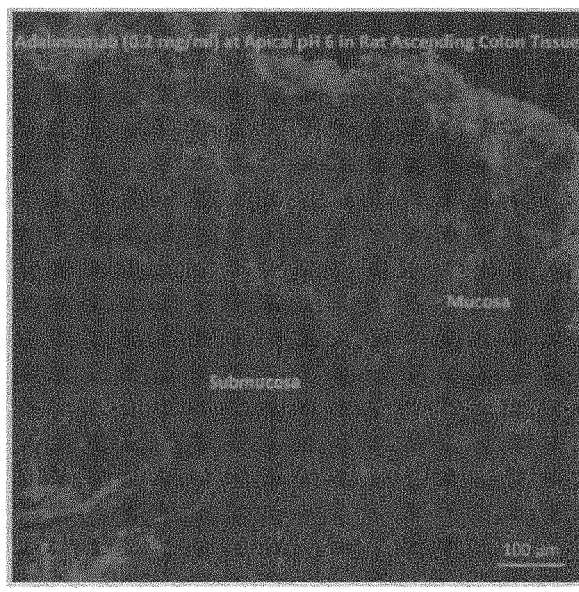
FIG. 15: CLSM of ascending rat colon tissue sections incubated with 0.2 mg/ml adalimumab antibodies at pH 6 or 7.4. Only antibody signal is shown. A) & B) Penetration of adalimumab in rat ascending colon tissue at apical pH 6. C) & D) Penetration of adalimumab in rat ascending colon tissue at apical pH 7.4.
Figure 15:
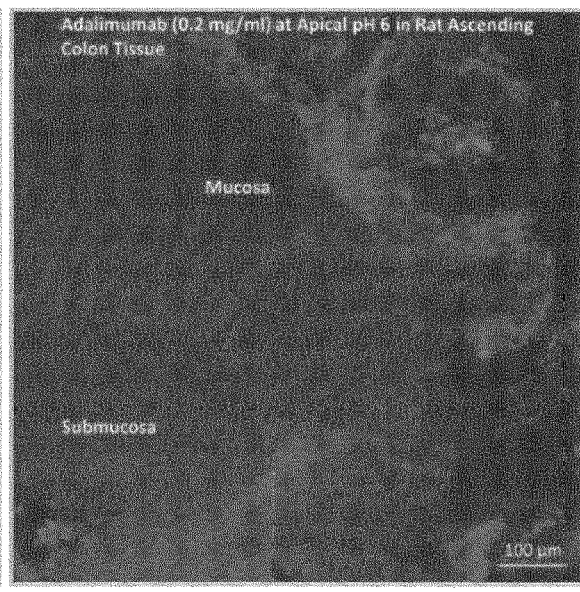
Figure 15:
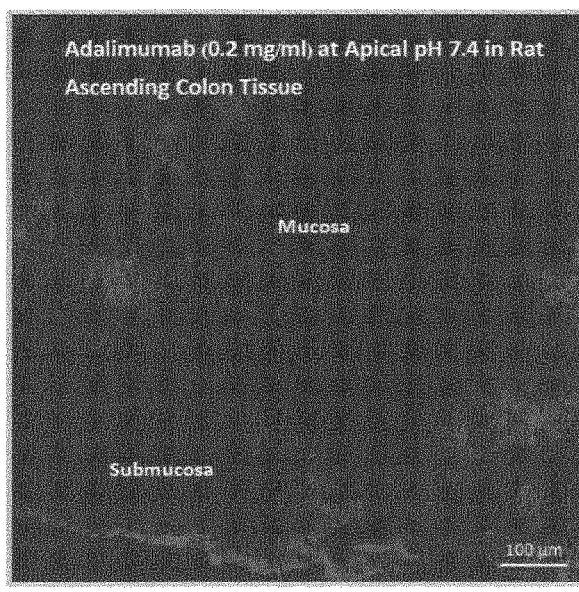
Figure 15:
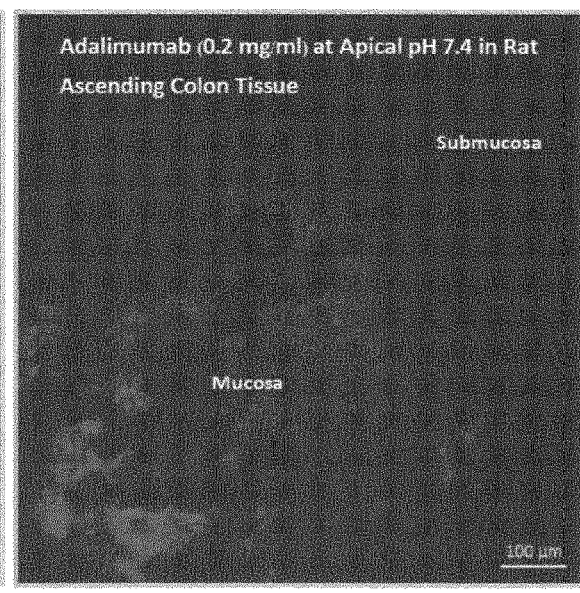

Effect of Luminal Acidic pH 6 on Colonic Tissue Transport of Infliximab and Adalimumab In the present example the effect of acidic luminal pH on the transport of Infliximab and adalimumab at a concentration of 0.2 mg/ml was explored at an apical pH of 6 and 7.4 respectively, in rat ascending colon tissue mounted on the Ussing chamber system. Following incubation, cryosectioning and staining with the secondary antibody, the tissue sections were analysed by confocal microscopy. FIGS. 14 and 15 show the transport of infliximab and adalimumab at apical pH 6 compared to pH 7.4. For both infliximab (FIG. 14) and adalimumab (FIG. 15), the drug signal was significantly higher in the mucosa of the colon tissue at apical pH 6 compared to pH 7.4. SEC analysis of samples from the basolateral compartment revealed that no drug permeated across the colon tissue into the basolateral compartment. Thus, a luminal pH that is acidic (pH-6) appears to enhance the penetration and localisation of infliximab and adalimumab in ascending colon tissue samples, compared to a neutral pH-7.4.

Example 10

Figure 16:
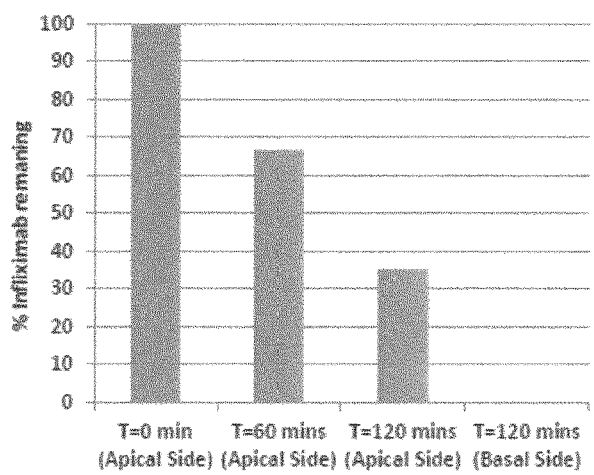
FIG. 16: % dose of A) infliximab and B) adalimumab remaining in the apical compartment at the end of 2 h incubation in the Ussing chamber with human colonic tissue sample.
Figure 16:
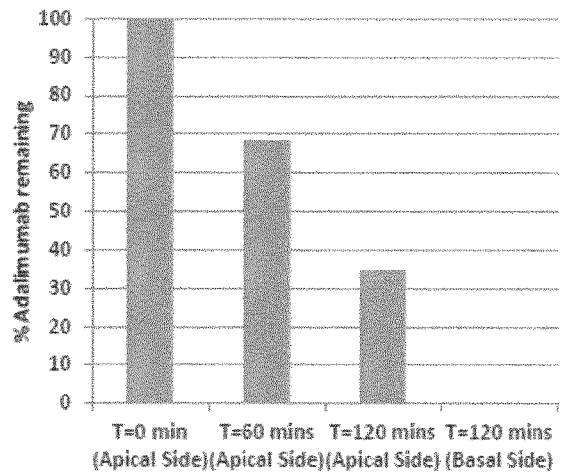
Figure 17:
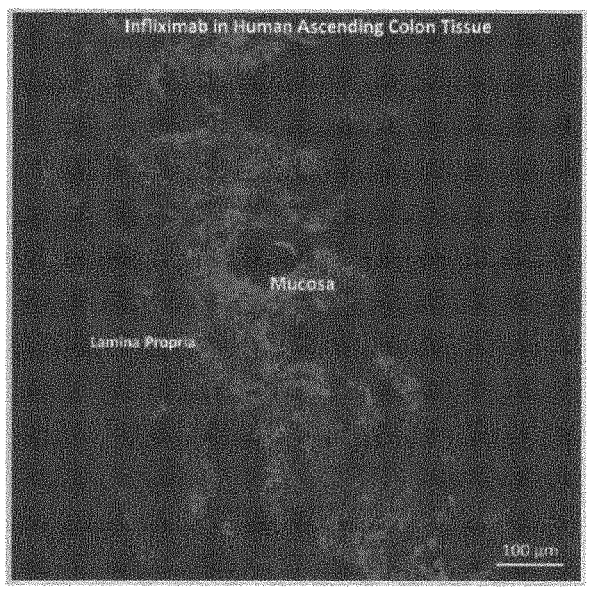
FIG. 17: A) & B) Localization of infliximab in the human colonic mucosa and lamina propria region. C) Human colonic mucosa control exposed to secondary antibody without exposure to infliximab.
Figure 17:
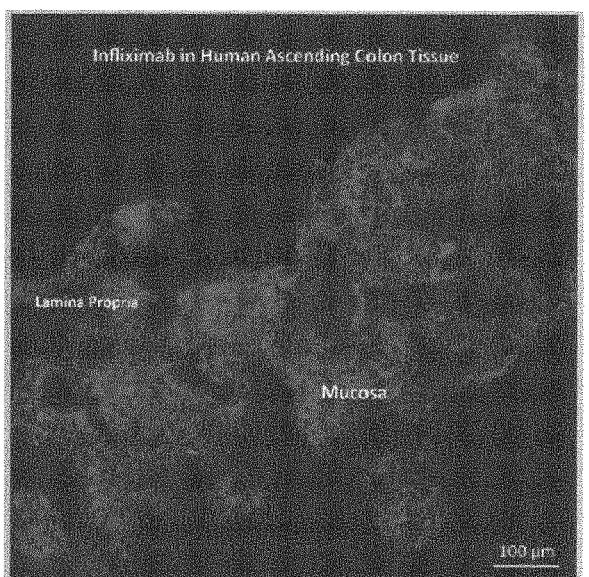
Figure 17:
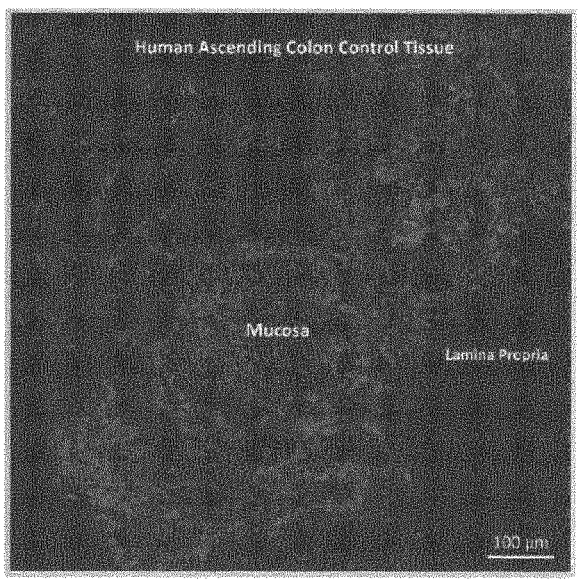

In the present example the uptake and penetration of infliximab and adalimumab were investigated in human tissue samples. The uptake and penetration studies of infliximab and adalimumab were conducted by mounting human tissue samples on Ussing chamber system and localization was analysed qualitatively using anti-human IgG secondary antibody detection method and further analysis by confocal laser scanning microscopy as used before in rodent models. The penetration of infliximab and adalimumab was tested at an apical concentration of 0.2 mg/ml and pH 7.4 for 2 h. The SE-HPLC data revealed that the antibody levels remaining in the apical compartment at the end of 2 h incubation in the Ussing chamber. For both infliximab and adalimumab, 35% of the dose was remaining at the end of 2 h (FIG. 16). No drug was detected by SE-HPLC in the basal compartment at the end of incubation. CLSM after the Ussing chamber experiment revealed that infliximab signal was detected both in the colonic mucosa and lamina propria region (FIG. 17), while adalimumab showed weaker signal in the mucosa region (data not shown). The control tissue sample without exposure to the mAbs did not show high interference with the anti-human secondary antibody.

Example 11

Formulation example: Enema (Adalimumab in tablet, to be reconstituted in vehicle) in two different strengths (100 mg and 80 mg Adalimumab, respectively).

TABLE 1

| Components | Quantity | Quantity | Function |
|---|---|---|---|
| Tablet | | | |
| Adalimumab (lyophilized) | 100 mg | 80 mg | Active ingredient |
| Microcrystalline cellulose | 372.5 mg | 392.5 mg | Binder |
| Polyvidone | 25 mg | 25 mg | Disintegrant |
| Magnesium stearate | 2.5 mg | 2.5 mg | Lubricant |
| Liquid for reconstitution | | | |
| Sodium citrate | 600 mg | 600 mg | pH modifier |
| Citric acid | 1130 mg | 1130 mg | pH modifier |
| Tris | 2190 mg | 2190 mg | pH modifier |
| Methyl parahydroxybenzoate | 80 mg | 80 mg | Preservative |
| Propyl parahydroxybenzoate | 20 mg | 20 mg | Preservative |
| Sodium chloride | 900 mg | 900 mg | For isotonicity |
| Water purified | 100 mL | 100 mL | Diluent |

This enema consists of two components: a dispersible tablet and a vehicle. The Adalimumab enema is reconstituted before use. The volume of the reconstituted enema is about 115 mL.

The above quantities refer to one unit. A suitable batch size for the manufacture is for example 1,000 units.

Manufacturing Instructions:

Tablet:

Step 1: Preparation of Pre-Mixture

Adalimumab and microcrystalline cellulose are mixed in a planetary mixer for about 10 minutes. Magnesium stearate is added through a 0.5 mm sieve and mixing is continued for 2 minutes.

Step 2: Final Mixing

Pre-mixture is added through a 1.0 mm sieve to a mixer and mixed for 20 minutes at high speed. Crosslinked polyvidone is added through a 0.75 mm sieve. Mixing is continued for another 10 minutes at the same speed. The mixture is transferred to an airtight container.

Step 3: Compression

Tabletting is performed on a rotary press at a relative humidity of <30%. Tablets are sampled for in-process control of tablet weight, disintegration, friability, crushing strength and tablet height.

Liquid for Reconstitution

Water purified is charged in a vessel. Methyl parahydroxybenzoate and propyl parahydroxybenzoate are added and dissolved while continuous stirring. Sodium chloride is added and dissolved during continuous stirring until the solution becomes homogenous. The bulk solution is filtered and filled into bottles.

Example 12

Formulation example: Ready to use Enema (Phosphate buffer) in two different strengths (100 mg and 80 mg Adalimumab, respectively).

TABLE 2

| Components | Quantity | Quantity | Function |
|---|---|---|---|
| Adalimumab | 100 mg | 80 mg | Active ingredient |
| Xanthan Gum | 650 mg | 650 mg | Stabilisator/Suspending agent |
| Citric acid | 300 mg | 300 mg | pH modifier |
| Sodium phosphate, dibasic | 980 mg | 980 mg | pH modifier |
| Sodium benzoate | 100 mg | 100 mg | Preservative |
| Water purified | 97.95 mL | 100 mL | Diluent |

The above quantities refer to one unit. A suitable batch size for the manufacture is for example 1,000 units.

Manufacturing of the bulk mixture (also applicable to other buffer systems):

Loading and adding the ingredients:

The purified water is loaded into a suitable stainless steel vessel equipped with a stirrer/homogenizer. Sodium benzoate and the buffer salts are added and the mixture is stirred and homogenized. Adalimumab is added to the stirred and homogenized solution. Xanthan gum is added, stirred and homogenized. The mixture is stirred, homogenized and gassed with nitrogen.

Filling:

The suspension is filled from the vessel (via filling hopper) into bottles by means of nitrogen pressure, filled to the target weight and closed with a cap. Filling and closing is carried out under nitrogen gassing.

Example 13

Formulation example: Ready to use Gel (Tris buffer) in two different strengths (100 mg and 80 mg Adalimumab, respectively).

TABLE 3

| Components | Quantity | Quantity | Function |
|---|---|---|---|
| Adalimumab | 100 mg | 80 mg | Active ingredient |
| Xanthan Gum | 2000 mg | 2000 mg | Stabilisator/Suspending agent |
| Sodium citrate | 600 mg | 600 mg | pH modifier |
| Citric acid | 1130 mg | 1130 mg | pH modifier |
| Tris | 2190 mg | 2190 mg | pH modifier |
| Sodium benzoate | 100 mg | 100 mg | Preservative |
| Water purified | 97.95 mL | 100 mL | Diluent |

The above quantities refer to one unit. A suitable batch size for the manufacture is for example 1,000 units.

Manufacturing of the bulk mixture (also applicable to other buffer systems):

Loading and adding the ingredients:

The purified water is loaded into a suitable stainless steel vessel equipped with a stirrer/homogenizer. Sodium benzoate and the buffer salts are added and the mixture is stirred and homogenized. Adalimumab is added to the stirred and homogenized solution. The mixture is stirred, homogenized and gassed with nitrogen. Xanthan gum is added, then stirred and homogenized until gelled. The mixture is gassed with nitrogen again.

Filling:

The suspension is filled from the vessel (via filling hopper) into bottles by means of nitrogen pressure, filled to the target weight and closed with a cap. Filling and closing is carried out under nitrogen gassing.

The invention claimed is:

1. A composition comprising (i) an active agent selected from the group consisting of antibodies specific to tumor necrosis factor alpha (TNFα) and functional fragments thereof and (ii) an amount of one or more suitable buffer agents and/or acidifiers effective to reduce the luminal pH in the large intestine, wherein said composition is formulated for rectal administration for use in the treatment of an inflammatory bowel disease in a human patient, further wherein administration of said composition results in the local accumulation of said active agent in the gastrointestinal wall and a decrease of a pH in the large intestinal lumen of said patient to between 5.5 and 6.5.

2. The composition according to claim 1, wherein said composition reduces the pH of a local microenvironment of the antibody or functional fragment thereof in the large intestinal lumen to between 5.5 and 6.5.

3. The composition according to claim 1, wherein the decrease of pH in the large intestinal lumen facilitates the uptake and/or penetration of the active agent into the gastrointestinal wall.

4. The composition according to claim 1, wherein said treatment results in a pH in the large intestinal lumen reading that is 6.5.

5. The composition according to claim 1, wherein said one or more suitable buffer agents and/or acidifiers effective to reduce the luminal pH in the large intestine is an acidifier selected from the group consisting of: acetic acid, adipic acid, ascorbic acid, citric acid, fumaric acid, itaconic acid, lactic acid, maleic acid, malic acid, phosphoric acid, propionic acid, succinic acid, sorbic acid and tartaric acid.

6. The composition according to claim 1, wherein said human patient afflicted with inflammatory bowel disease is in remission or, alternatively, suffers from a mild or moderate form of the inflammatory bowel disease.

7. The composition according to claim 1, wherein said treatment results in a concentration of the anti-TNFα antibody or functional fragment thereof in the large intestinal lumen of said human patient being treated in the range of 0.02 to 1 mg/ml.

8. The composition according to claim 1, wherein the functional antibody fragment specific to TNFα is selected from the group consisting of: a Fab fragment, a F(ab')2 fragment, a Fab' fragment, an scFv, a dsFv, a VHH, a diabody, a triabody, a tetrabody, an Fc fusion protein and a minibody.

9. The composition according to claim 1, wherein the pH in the large intestinal lumen of the human patient before the treatment is higher than 6.5.

10. The composition according to claim 1, wherein said treatment results in a pH in the large intestinal lumen that ranges from 5.7 to 6.3.

11. The composition according to claim 1, wherein said treatment results in a pH in the large intestinal lumen that ranges from 5.9 to 6.1.

12. The composition according to claim 1, wherein said treatment results in a concentration of the anti-TNFα antibody or functional fragment thereof in the large intestinal lumen of said human patient being treated in the range of 0.2 to 0.8 mg/ml.

13. The composition according to claim 1, wherein said composition is in the form of an enema, a gel, a foam or a suppository.

* * * * *